US008735354B2

(12) United States Patent
Jun et al.

(10) Patent No.: US 8,735,354 B2
(45) Date of Patent: May 27, 2014

(54) ENDOTHELIUM MIMICKING NANOMATRIX

(75) Inventors: Ho-Wook Jun, Hoover, AL (US); Meenakshi Kushawaha, Birmingham, AL (US); Brigitta C. Brott, Columbiana, AL (US); Peter Anderson, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 548 days.

(21) Appl. No.: 12/497,305

(22) Filed: Jul. 2, 2009

(65) Prior Publication Data

US 2010/0119573 A1  May 13, 2010

Related U.S. Application Data

(60) Provisional application No. 61/112,578, filed on Nov. 7, 2008.

(51) Int. Cl.
  *A61K 38/10* (2006.01)
  *A61K 9/00* (2006.01)
  *C07K 7/08* (2006.01)
  *C07K 1/107* (2006.01)

(52) U.S. Cl.
  USPC .......................... 514/16.1; 530/327; 530/333

(58) Field of Classification Search
  None
  See application file for complete search history.

(56) References Cited

U.S. PATENT DOCUMENTS

| | | | |
|---|---|---|---|
| 7,713,923 B2 | 5/2010 | Genove et al. | 514/2 |
| 8,114,431 B2 | 2/2012 | Garcia et al. | 424/423 |
| 8,114,834 B2 | 2/2012 | Hsu et al. | 514/3.2 |
| 2005/0181973 A1 | 8/2005 | Genove et al. | 514/2 |
| 2007/0293927 A1 | 12/2007 | Frank et al. | 623/1.15 |
| 2008/0175883 A1* | 7/2008 | Hsu et al. | 424/423 |

FOREIGN PATENT DOCUMENTS

| | | |
|---|---|---|
| CN | 102355904 | 2/2012 |
| EP | 2365820 | 9/2011 |
| JP | 2012-508255 | 4/2012 |
| WO | WO 2008/067145 | 6/2008 |
| WO | WO 2010/054316 | 5/2010 |

OTHER PUBLICATIONS

Jun H-W, Kushwaha M, Anderson J, Minor W, Andukuri A, Bosworth C, Lancaster J, Brott B, Anderson P, "Abstract 4928: Natural Endothelium Mimicking Self-Assembled Nanomatrix for Drug Eluting Stent Applications," Circulation, 2008, 118: S_962, Abstract only.*
Jun H-W, Yuwono V, Paramonov SE, Hargerink JD, "Enzyme-Mediated Degradation of Peptide-Amphiphile Nanofiber Networks," Advanced Materials, 2005, 17: 26122617.*
Paramonov SE, Jun H-W, Hargerink JD, "Modulation of Peptide Amphiphile Nanofibers via Phospholipid Inclusions," Biomacromolecules, 2006, 7: 24-26.*
European Search Report issued Dec. 19, 2012 by the European Patent Office for Application No. 9825552 filed Nov. 9, 2009 (Applicant—UAB Research Foundation // Inventor—Jun, et al.; (pp. 1-11).
Amendment filed May 31, 2011 to the European Patent Office for Application No. 9825552 filed Nov. 9, 2009 (Applicant—UAB Research Foundation // Inventor—Jun, et al.; (pp. 1-6).
European Office Action issued Aug. 17, 2011 by the European Patent Office for Application No. 9825552 filed Nov. 9, 2009 (Applicant—UAB Research Foundation // Inventor—Jun, et al.; (pp. 1-2).
Amendments filed Oct. 13, 2011 to the Japanese Patent Office for Application No. 2011535727 filed Nov. 9, 2009 (Applicant—UAB Research Foundation // Inventor—Jun, et al.; (pp. 1-8).
International Preliminary Report on Patentability issued May 10, 2011 by the International Searching Authority for Application No. PCT/US2009/063732 filed Sep. 11, 2009 (Applicant—UAB Research Foundation // Inventor—Jun, et al.; (pp. 1-6).
International Search Report issued May 6, 2010 by the International Searching Authority for Application No. PCT/US2009/063732 filed Sep. 11, 2009 (Applicant—UAB Research Foundation // Inventor—Jun, et al.; (pp. 1-4).
Written Opinion issued May 6, 2010 by the International Searching Authority for Application No. PCT/US2009/063732 filed Sep. 11, 2009 (Applicant—UAB Research Foundation // Inventor—Jun, et al.; (pp. 1-5).
Acharya G, Park K. Mechanisms of controlled drug release from drug-eluting stents. Adv Drug Deliv Rev. 2006; 58:387-401.
Aicher A, Heeschen C, Mildner-Rihm C, Urbich C, Ihling C, Technau-Ihling K, Zeiher AM, Dimmeler S. Essential role of endothelial nitric oxide synthase for mobilization of stem and progenitor cells. Nat Med. 2003; 9(11):1370-1376.
Alsberg E, Kong HJ, Hirano Y, Smith MK, Albeiruti A, Mooney DJ. Regulating bone formation via controlled scaffold degradation. J Dental Res. 2003; 82(11):903-908.
Anderson JM, et al. Modulating the gelation properties of self-assembling peptide amphiphiles. ACS Nano, American Chemical Society. 2009; 3(11): 3447-3454.
Babapulle MN, Joseph L, Belisle P, Brophy JM, Eisenberg MJ. A hierarchical Bayesian meta-analysis of randomized clinical trials of drug-eluting stents. Lancet. 2004; 364(9434):583-591.
Barnes CP, Sell SA, Boland ED, Simpson DG, Bowlin GL. Nanofiber technology: designing the next generation of tissue engineering scaffolds. Adv Drug Deliv Rev. 2007; 59(14):1413-1433.
Bauters C, Isner JM. The biology of restenosis. Prog Cardiovasc Dis. 1997;40(2):107-116.
Beck K, Hunter I, Engel J. Structure and function of laminin: anatomy of a multidomain glycoprotein. Faseb J. 1990; 4(2):148-160.

(Continued)

Primary Examiner — Julie Ha
(74) Attorney, Agent, or Firm — Ballard Spahr LLP

(57) ABSTRACT

Disclosed herein are peptide amphiphiles for use in producing a natural endothelium mimicking nanomatrix. The disclosed natural endothelium mimicking nanomatrix can be used to coat medical devices such as vascular stents to promote endothelializaiton and inhibit restenosis and thrombosis. This abstract is intended as a scanning tool for purposes of searching in the particular art and is not intended to be limiting of the present invention.

19 Claims, 15 Drawing Sheets

(56) References Cited

OTHER PUBLICATIONS

Bohl KS, West JL. Nitric oxide-generating polymers reduce platelet adhesion and smooth muscle cell proliferation. Biomaterials. 2000; 21:2273-2278.

Bryant SJ, Anseth KS. Hydrogel properties influence ECM production by chondrocytes photoencapsulated in poly(ethylene glycol) hydrogels. J Biomed Mater Res. 2002; 59:63-72.

Camenzind E, Steg PG, Wijns W. Stent thrombosis late after implantation of first-generation drug-eluting stents. Circulation. 2007; 7(115):1440-1455.

Chen K, Pittman RN, Popel AS. Nitric oxide in the vasculature: where does it come from and where does it go? A quantitative perspective. Antioxid Redox Signal. 2008; 10(7):1185-1198.

Colombo A, Chieffo A. Drug-eluting stent update 2007: Part III: Technique and unapproved/unsettled indications (left main, bifurcations, chronic total occlusions, small vessels and long lesions, saphenous vein grafts, acute myocardial infarctions, and multivessel disease). Circulation. 2007; 116:1424-1432.

Curtis A, Wilkinson C. Nanotechniques and approaches in biotechnology. Trends Biotechnol. 2001; 19(3):97-101.

Davies KM, Wink DA, Saavedra JE, Keefer LK. Chemistry of the diazeniumdiolates. 2. kinetics and mechanism of dissociation to nitric oxide in aqueous solution. J Am Chem Soc.2001; 123:5473-5481.

de Man FH, Stella PR, Nathoe H, Kirkels H, Hamer B, Meijburg HW, Doevendans PA. Stent thrombosis in real-world patients: a comparison of drug-eluting with bare metal stents. Neth Heart J. 2007; 15(11):382-386.

Do Y, Kao E, Ganaha F, Minamiguchi H, Sugimoto K, Lee J, Elkins C, Amabile P, Kuo M, Wang D, Waugh J, Dake M. In-stent restenosis limitation with stent-based controlled-release nitric oxide: Initial results in rabbits. Radiology. 2004; 230:377-382.

Dobesh PP, Stacy ZA, Ansara AJ, Enders JM. Drug-eluting stents: a mechanical and pharmacologic approach to coronary artery disease. Pharmacotherapy.2004; 24(11):1554-1577.

Finn A, Nakazawa G, Joner M, Kolodgie F, Mont E, Gold H, Virmani R. Vascular responses to drug eluting stents: importance of delayed healing. Arterioscler Thromb Vasc Biol. 2007; 27(7):1500-1510.

Fittkau MH, Zilla P, Bezuidenhout D, Lutolf MP, Human P, Hubbell JA, Davies N. The selective modulation of endothelial cell mobility on RGD peptide containing surfaces by YIGSR peptides. Biomaterials. 2005; 26(2):167-174.

Giannelli G, Falk-Marzillier J, schiraldi O, Stetler-Stevenson WG, Quaranta V. Induction of cell migration by matrix metallopretease-2 cleavage of laminin-5 Science. 1997; 277:225-228.

Gori T, Parker JD. The puzzle of nitrate tolerance: pieces smaller than we thought? Circulation. 2002; 106(18):2404-2408.

Hanson SR, Hutsell TC, Keefer LK, Mooradian DL, Smith DJ. Nitric oxide donors: a continuing opportunity in drug design. Adv Pharmacol .1995; 34:383-398.

Hartgerink JD, Baniash E, Stupp SI. Peptide-amphiphile nanofibers: A versatile scaffold for the preparation of self-assembling materials. Proc Natl Acad Sci. 2002; 99(8):5133-5138.

Hartgerink JD, Beniash E, Stupp SI. Self-assembly and mineralization of peptide-amphiphile nanofibers. Science. 2001; 294:1684-1688.

Hosseinkhani H, Hosseinkhani M, Khademhosseini A, Kobayashi H, Tabata Y. Enhanced angiogenesis through controlled release of basic fibroblast growth factor from peptide amphiphile for tissue regeneration. Biomaterials. 2006; 27(34):5836-5844.

Hosseinkhani H, Hosseinkhani M, Tian F, Kobayashi H, Tabata Y. Bone regeneration on a collagen sponge self-assembled peptide-amphiphile nanofiber hybrid scaffold. Tissue Eng. 2007; 13(1):11-19.

Hosseinkhani H, Hosseinkhani M, Tian F, Kobayashi H, Tabata Y. Ectopic bone formation in collagen sponge self-assembled peptide-amphiphile nanofibers hybrid scaffold in a perfusion culture bioreactor. Biomaterials. 2006; 27(29):5089-5098.

Hou D, Narciso H, Kamdar K, Zhang P, Barclay B, March KL. Stent-based nitric oxide delivery reducing neointimal proliferation in a porcine carotid overstretch injury model. Cardiovasc Intervent Radiol. 2005; 28(1):60-65.

Hrabie JA, Keefer LK. Chemistry of the nitric oxide-releasing diazeniumdiolate ("nitrosohydroxylamine") functional group and its oxygen-substituted derivatives. Chem Rev. 2002; 102(4):1135-1154.

Hubbell JA, Massia SP, Desai NP, Drumheller PD. Endothelial cell-selective materials for tissue engineering in the vascular graft via a new receptor. Bio/Technology. 1991; 9:568-572.

Jun et al. Abstract 4928: Natural Endothelium Mimicking Self-Assembled Nanomatrix for Drug 1-12 Eluting Stent Applications. Circulation: 118:5_962 (Oct. 28, 2008); Abstract.

Jun H, West J. Development of a YIGSR-peptide-modified polyurethaneurea to enhance endothelialization. J Biomater Sci Polymer Edn. 2004; 15(1):73-94.

Jun H, West J. Modification of polyurethaneurea with PEG and YIGSR peptide to enhance endothelialization without platelet adhesion. J Biomed Mater Res Part B: Appl Biomater. 2005; 72B:131-139.

Jun HW, Taite LJ, West JL. Nitric oxide-producing polyurethanes. Biomacromolecules. 2005; 6:838-844.

Jun HW, Yuwono V, Paramonov SE, Hartgerink JD. Enzyme-mediated degradation of peptide-amphiphile nanofiber networks. Adv Mater. 2005; 17:2612-2617.

Kaul S, Makkar RR, Nakamura M, Litvack FI, Shah PK, Forrester JS, Hutsell TC, Eigler NL. Inhibition of acute stent thrombosis under high-shear flow conditions by a nitric oxide donor, DMHD/NO. An ex vivo porcine arteriovenous shunt study. Circulation. 1996; 94(9):2228-2234.

Kawasaki K, Smith RS, Jr., Hsieh CM, Sun J, Chao J, Liao JK. Activation of the phosphatidylinositol 3-kinase/protein kinase Akt pathway mediates nitric oxide-induced endothelial cell migration and angiogenesis. Mol Cel Biol. 2003; 23(16):5726-5737.

Keefer LK, Nims RW, Davies KM, Wink DA. "NONOates" (1-substituted diazen-1-ium-1,2-diolates) as nitric oxide donors: convenient nitric oxide dosage forms. Methods Enzymol. vol. 268; 1996:281-293.

Kolodgie FD, John M, Khurana C, Farb A, Wilson PS, Acampado E, Desai N, Soon-Shiong P, Virmani R. Sustained reduction of in-stent neointimal growth with the use of a novel systemic nanoparticle paclitaxel. Circulation. 2002; 106:1195-1198.

Kotani J, Awata M, Nanto S, Uematsu M, Oshima F, Minamiguchi H, GS GSM, Nagata S. Incomplete neointimal coverage of sirolimus-eluting stents: angioscopic findings. J Am Coll Cardiol 2006; 47(10):2108-2111.

Kuo PC, Schroeder RA. The emerging multifaceted roles of nitric oxide. Ann Surg. 1995; 221(3):220-235.

Leon MB. Late thrombosis a concern with drug-eluting stents. J Interv Cardiol. 2007; 20(1):26-29.

Lipke EA, West JL. Localized delivery of nitric oxide from hydrogels inhibits neointima formation in a rat carotid balloon injury model. Acta Biomaterialia. 2005; 1(6):597-606.

Liuzzo JP, Ambrose JA, Coppola JT. Sirolimus- and taxol-eluting stents differ towards intimal hyperplasia and re-endothelialization. J Invasive Cardiol. 2005; 17(9):497-502.

Lowik D, Hest JCMv. Peptide based amphiphiles. Chem Soc Rev. 2004; 33:234-245.

Malkar NB, Lauer-Fields JL, Juska D, Fields GB. Characterization of peptide-amphiphiles possessing cellular activation sequences. Biomacromolecules. 2003; 4(3):518-528.

Marin J, Rodriguez-Martinez MA. Role of vascular nitric oxide in physiological and pathological conditions. Pharmacol Ther. 1997; 75(2):111-134.

Massia SP, Hubbell JA. Human endothelial cell interactions with surface-coupled adhesion peptides on a nonadhesive glass substrate and two polymeric biomaterials. J Biomed Mater Res. 1991; 25(2):223-242.

Massia SP, Rao SS, Hubbell JA. Covalently immobilized laminin peptide Tyr-Iie-Gly-Ser-Arg (YIGSR) supports cell spreading and co-localization of the 67-kilodalton laminin receptor with a-actin and vinculin. J Biol Chem. 1993; 268:8053-8059.

(56) References Cited

OTHER PUBLICATIONS

Melikian N, Wijns W. Drug-eluting stents: a critique. Heart. 2008;94:145-152.
Miller M, Megson I. Recent developments in nitric oxide donor drugs. Br J Pharmacol. 2007; 151(3):305-321.
Morice MC, Serruys PW, Sousa JE, Fajadet J, Ban Hayashi E, Perin M, Colombo A, Schuler G, Barragan P, Guagliumi G, Molnar F, Falotico R. A randomized comparison of a sirolimus-eluting stent with a standard stent for coronary revascularization. N Engl J Med. 2002; 346(23):1773-1780.
Moses JW, Leon MB, Popma JJ, Fitzgerald PJ, Holmes DR, O'Shaughnessy C, Caputo RP, Kereiakes DJ, Williams DO, Teirstein PS, Jaeger JL, Kuntz RE. Sirolimus-eluting stents versus standard stents in patients with stenosis in a native coronary artery. N Engl J Med. 2003; 349(14):1315-1323.
Ozaki Y, Violaris AG, Serruys PW. New stent technologies. Prog Cardiovasc Dis. 1996;39(2):129-140.
Paramonov SE, Jun H, Hartgerink JD. Modulation of Peptide—Amphiphile via Phospholipid Inclusions. Biomacromolecules 2006, 7 : 24-26.
Pulfer SK, Ott D, Smith DJ. Incorporation of nitric oxide-releasing cross-linked polyethyleneimine microspheres into vascular grafts. J Biomed Mater Res. 1997; 37(2):182-189.
Rajangam K, Behanna HA, Hui MJ, Han X, Hulvat JF, Lomasney JW, Stupp SI. Heparin binding nanostructures to promote growth of blood vessels. Nano Lett. 2006; 6(9):2086-2090.
Rao SV, Shaw RE, Brindis RG, Klein LW, Weintraub WS, Peterson ED. On-versus off-label use of drug-eluting coronary stents in clinical practice (report from the American College of Cardiology National Cardiovascular Data Registry [NCDR]). Am J Cardiol. 2006; 97(10):1478-1481.
Reynolds MM, Frost MC, Meyerhoff ME. Nitric oxide-releasing hydrophobic polymers: preparation, characterization, and potential biomedical applications. Free Radic Biol Med. 2004; 37(7):926-936.
Roiron C, Sanchez P, Bouzamondo A, Lechat P, Montalescot G. Drug eluting stents: an updated meta-analysis of randomized controlled trials. Heart. 2006; 92(5):641-649.
Rosamond, et al. Heart Disease and Stroke Statistics—2007 Update. Circulation. 2007; 115:e69-e171.
Sargeant TD, Guler MO, Oppenheimer SM, Mata A, Satcher RL, Dunand DC, Stupp SI. Hybrid bone implants: self-assembly of peptide amphiphile nanofibers within porous titanium. Biomaterials. 2008; 29(2):161-171.
Steffel J, Tanner FC. Biological effects of drug-eluting stents in the coronary circulation. Herz. 2007; 32(4):268-273.
Taite LJ, Yang P, Jun HW, West JL. Nitric oxide-releasing polyurethane-PEG copolymer containing the YIGSR peptide promotes endothelialization with decreased platelet adhesion. J Biomed Mater Res B Appl Biomater. 2008; 84(1):108-116.
Van Belle E, Susen S, Jude B, Bertrand ME. Drug-eluting stents: trading restenosis for thrombosis? J Thromb Haemost. 2007;5 Suppl 1:238-245.
Verma S, Marsden P. Nitric oxide-eluting polyurethanes- vascular grafts of the future? New Engl J Med. 2005; 353(7):730-731.
Violaris AG, Ozaki Y, Serruys PW. Endovascular stents: a 'break through technology', future challenges. Int J Card Imaging. 1997;13(1):3-13.
Webster MW, Ormiston JA. Drug-eluting stents and late stent thrombosis. Lancet. 2007; 370(9591):914-915.
Wessely R, Schomig A, Kastrati A. Sirolimus and Paclitaxel on polymer-based drug-eluting stents: similar but different. J Am Coll Cardiol. 2006; 47(4):708-714.
Win HK, Caldera AE, Maresh K, Lopez J, Rihal CS, Parikh MA, Granada JF, Marulkar S, Nassif D, Cohen DJ, Kleiman NS. Clinical outcomes and stent thrombosis following off-label use of drug-eluting stents. JAMA. 2007; 297(18):2001-2009.
Windecker S, Meier B. Intervention in coronary artery disease. Heart. 2000; 83:481-490.
Ziche M, Morbidelli L, Masini E, Amerini S, Granger HJ, Maggi CA, Geppetti P, Ledda F. Nitric oxide mediates angiogenesis in vivo and endothelial cell growth and migration in vitro promoted by substance P. J Clin Invest. 1994; 94(5):2036-2044.
Zimarino M, Renda G, De Caterina R. Optimal duration of antiplatelet therapy in recipients of coronary drug-eluting stents. Drugs. 2005; 65(6):725-732.
Claims filed with Response to Official Action filed Feb. 14, 2014 for Japanese Patent Application No. 2011-535727, which claims priority to PCT/US2009/063732, filed Nov. 9, 2009 (UAB Res. Foundation—Applicant//Ho-Wook Jun et al.—Inventors) (10 pages).

* cited by examiner

A.

B. $X^- + 2NO \rightarrow X\text{-}[N(O)NO]^-$

C. $X\text{-}[N(O)NO]^- \rightarrow X^- + 2NO$

D.

ENDOTHELIUM MIMICKING NANOMATRIX

CROSS-REFERENCE TO RELATED APPLICATIONS

This application claims benefit of U.S. Provisional Application No. 61/112,578, filed Nov. 7, 2008, which is hereby incorporated herein by reference in its entirety.

BACKGROUND

Cardiovascular diseases (CVDs) are the number one cause of death in U.S. They claim approximately one million lives and more than 400 billion US Dollars every year. The main cause of CVDs is arterial obstruction by the deposition of cholesterol in the inner lining of the artery. This is termed atherosclerosis (Silverthorn D U. 2004).

For the treatment of atherosclerosis, a non-invasive technique called balloon angioplasty was introduced in 1970s, which provided an attractive alternative to coronary artery bypass grafting. It used a slender collapsed balloon catheter that is inserted and inflated at the site of plaque. Upon inflation, the balloon compresses and ruptures the plaque, removing the blockage. This technique provided immediate relief to the patient. However, it was limited by the problem of abrupt closure of the artery after withdrawal of the catheter (Windecker S, et al. 2000). These challenges lead to the design of new biomedical solutions, such as bare metal stents.

To prevent the abrupt closure of artery, lattice-shaped expandable metal tubes known as bare metal stents (BMS) were introduced in 1990s. A balloon tipped catheter with a collapsed stent is inserted with a guiding catheter and guide wire. When the balloon is inflated at the plaque site, the stent expands, locks in place, and forms a scaffold holding the artery open. The use of BMS reduced the rate of restenosis compared to balloon angioplasty. While they were successful in preventing elastic recoil of the artery, BMS suffered from the problem of restenosis (i.e. re-closure of the artery) (Sheiban I, et al. 2002).

FIG. 1 shows a schematic representation of the principle mechanisms of restenosis, which include elastic recoil, negative vessel remodeling, and neointimal proliferation (Dobesh P P, et al. 2004). BMS virtually eliminates the problem of elastic recoil (Sheiban I, et al. 2002, Ozaki Y, et al. 1996) and negative vessel remodeling (Sheiban I, et al. 2002). However, the main mechanism of restenosis in BMS is neointimal hyperplasia (Violaris A G, et al. 1997). Neointimal hyperplasia is caused by endothelial denudation due to the penetration of stent struts into the vessel wall. It can be imagined that the fractured plaque exposes the thrombogenic contents of the vessel wall to the lumen, leading to a cascade of platelet adhesion, activation, and thrombosis. In addition, endothelial denudation results in the loss of antithrombotic factors. Activated platelets release factors that favor smooth muscle cell proliferation and migration. Meanwhile, smooth muscle cells also change their morphology from contractile to synthetic. This can result in smooth muscle cell migration and increased extracellular matrix (ECM) synthesis, which leads to neointimal hyperplasia and in-stent restenosis (Bauters C, et al. 1997). Hence, BMS remained limited by the high rates of in-stent restenosis. Thus, further advancements to the biomedical design of BMS were needed, such as the incorporation of localized drug delivery.

The major challenge of catheter-based drug delivery is to achieve the localization of drugs at the site of vascular injury in order to reduce the formation of neointimal hyperplasia. Thus, controlled drug delivery systems have been applied to stents, resulting in the development of drug eluting stents (DES). DES became commercially available in U.S. in 2003 (Ong A T, et al. 2005). They are coated with single or multiple bioactive agents, which are delivered in blood stream and surrounding tissues after implantation. These stents are designed to release drugs that interfere with the process of neointimal hyperplasia by targeting its biochemical pathways. Several drug delivery strategies such as diffusion controlled, dissolution/degradation controlled, and ion exchange-based methods have been investigated for DES (Acharya G, et al. 2006). DES have been shown to reduce restenosis compared with BMS (de Man F H, et al. 2007). They have been implanted in more than 6 million patients from 2004 to 2006 (Colombo A, et al. 2007).

The stent market is shared by only two drug-eluting stents: (1) Cordis CYPHER™, sirolimus-eluting stent and (2) Boston Scientific TAXUS™, paclitaxel-eluting stent. (FDA approved the CYPHER™ stent in April 2003 and TAXUS™ stent in March 2004). Both sirolimus and paclitaxel work by inhibiting the cell cycle. Sirolimus is an immunosuppressive drug that promotes kinase activation, leading to the inhibition of the cellular growth phase. Paclitaxel binds to microtubules in dividing cells and causes them to assemble, thereby preventing mitosis (Wessely R, et al. 2006). Use of these DES has shown to reduce the risk of restenosis by at least 80%, as shown by numerous randomized controlled trials (Morice M C, et al. 2002; Moses J W, et al. 2003) and meta-analyses (Roiron C, et al. 2006). However, no difference in mortality rate has been observed between DES and BMS (Roiron C, et al. 2006; Babapulle M N, et al. 2004). This can be attributed to the occurrence of late stent thrombosis or blood clots, which is an emerging cause of concern in the first generation of DES (Camenzind E, et al. 2007; Webster M W, et al. 2007; Van Belle E, et al. 2007; Jaffe R, et al. 2007; Leon M B. 2007). This late thrombosis seems to be related to discontinued antiplatelet therapy, (Zimarino M, et al. 2005) rare cases of local hypersensitivity as a reaction to the drug, and "off-label use" of DES (Win H K, et al. 2007). According to FDA standards, DES have only been approved for patients with previously untreated coronary stenosis of less than 30 mm in length and a reference vessel diameter within the range from 2.50 mm to 3.70 mm (Win H K, et al. 2007; Melikian N, et al. 2006). A study from American College of Cardiology reported "off-label use" is common and has increased in frequency over time (Rao S V, et al. 2006). In addition, studies have shown that DES cause significant delay in arterial healing due to persistent fibrin deposition and poor endothelialization when compared with the sites of BMS implantation (Finn A, et al. 2007). Angioscopic findings show incomplete neointimal covering of sirolimus-eluting stents (Kotani J, et al. 2006). Also, patient risk factors like diabetes, renal failure, and previous complications have contributed to the incidences of late thrombosis in the patients who received DES (Jaffe R, et al. 2007).

These concerns have given way to the idea of an ideal stent which should be designed to control and direct vessel repair after surgery without eliciting undesirable inflammatory response and eventually leading to a re-endothelialized vessel wall.

BRIEF SUMMARY

In accordance with the purpose of this invention, as embodied and broadly described herein, this invention relates to peptide amphiphiles for use in producing a natural endothelium mimicking nanomatrix. The disclosed natural endothelium mimicking nanomatrix can be used to coat medical devices such as vascular stents. Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 7A shows HUVECs attain their regular spread morphology within 2 hours. FIG. 7B shows AoSMCs remain round in shape.

DETAILED DESCRIPTION

Figure 1:
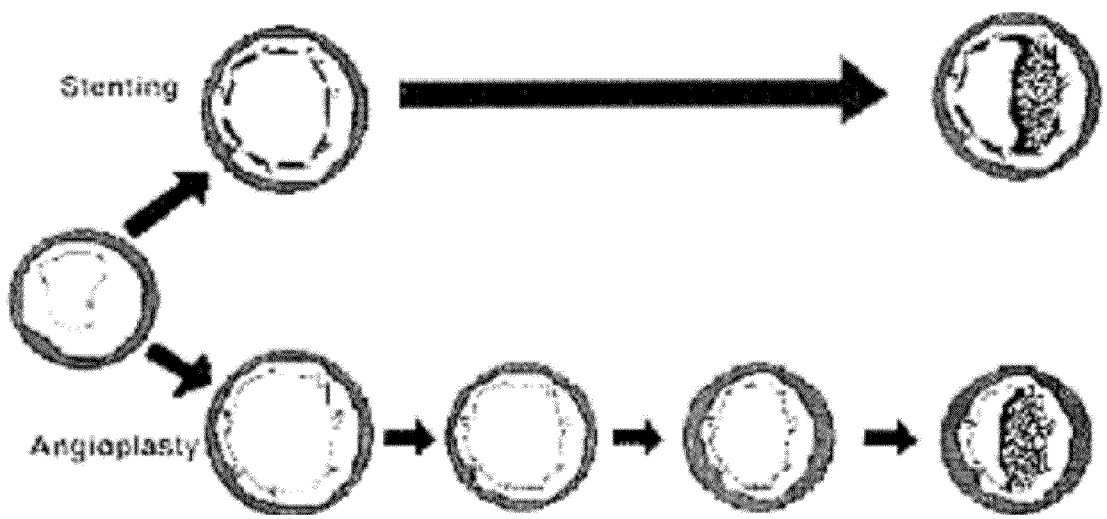
FIG. 1 shows mechanisms and timelines of restenosis. Neointimal proliferation is the main cause of restenosis in bare metal stents (BMS). See Dobesh, P. P., et al. (2004). Pharmacotherapy. 24 (11): 1554-77.
Figure 2:
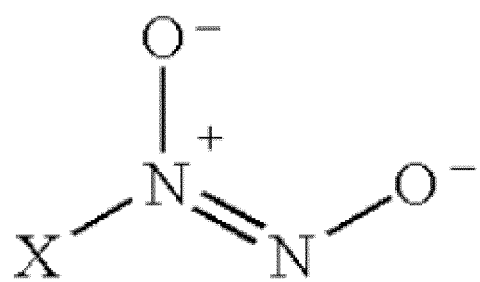
FIG. 2A shows chemical structure of diazeniumdiolates.
FIG. 2B shows formation of diazeniumdiolates by reaction of a nucleophilic amine (X—) with NO.
FIG. 2C shows dissociation of diazoniumdiolates on protonation to release free NO.
FIG. 2D shows structure of Lysine. It has two pendant amine groups for NO binding.
Figure 2:
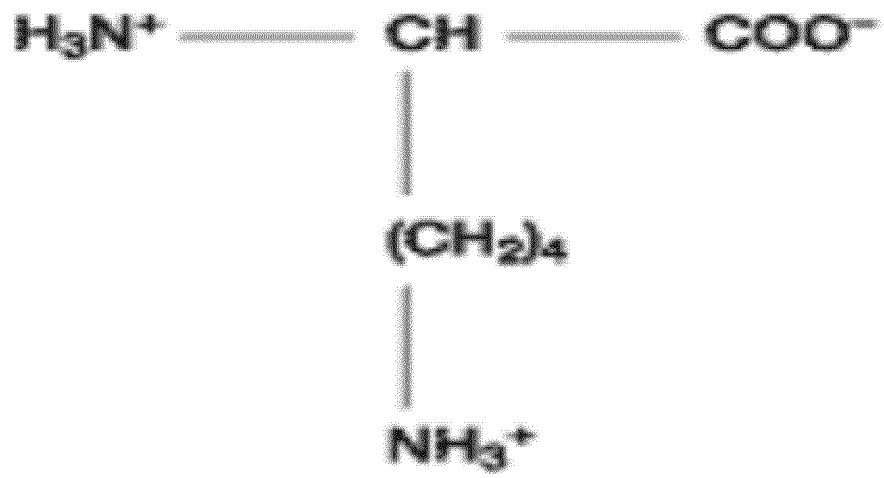
Figure 3:
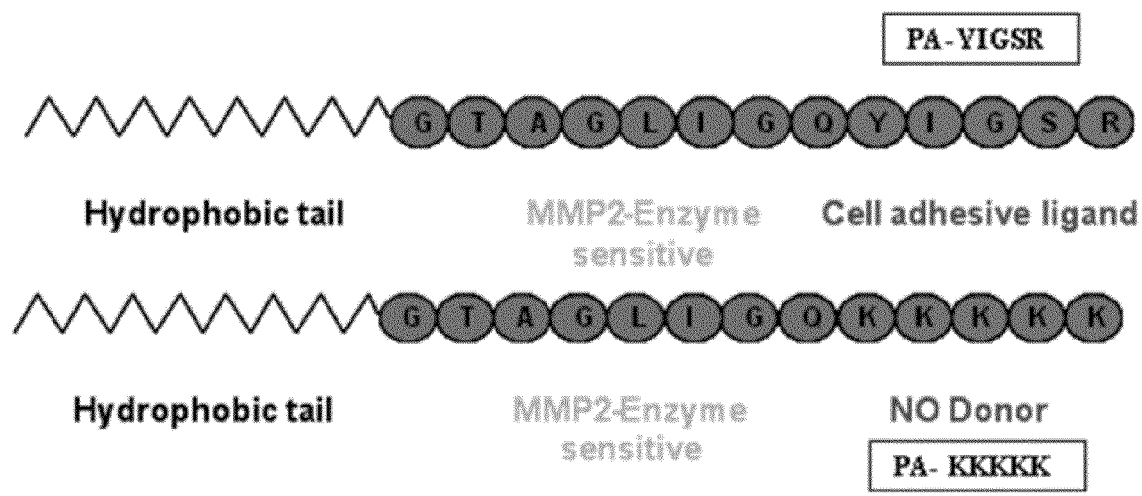
FIG. 3 shows molecular structure of PAs. YIGSR (SEQ ID NO:2) is a cell adhesive ligand and KKKKK (SEQ ID NO:3) is a NO donor.

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation. The discussion of references states what their authors assert, and Applicant reserves the right to challenge the accuracy and pertinency of the cited documents.

A. DEFINITIONS

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "effective amount" refers to an amount that is sufficient to achieve a desired result or to have an effect on undesired symptoms, but is generally insufficient to cause adverse side affects. The specific effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In a further aspect, a preparation can be administered in a "diagnostically effective amount"; that is, an amount effective for diagnosis of a disease or condition. In a further aspect, a preparation can be administered in a "therapeutically effective amount"; that is, an amount effective for treatment of a disease or condition. In a further aspect, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "biologically active agent" or "bioactive agent" means an agent that is capable of providing a local or systemic biological, physiological, or therapeutic effect in the biological system to which it is applied. For example, the bioactive agent can act to control infection or inflammation, enhance cell growth and tissue regeneration, control tumor growth, act as an analgesic, promote anti-cell attachment, and enhance bone growth, among other functions. Other suitable bioactive agents can include anti-viral agents, hormones, antibodies, or therapeutic proteins. Other bioactive agents include prodrugs, which are agents that are not biologically active when administered but, upon administration to a subject are converted to bioactive agents through metabolism or some other mechanism. Additionally, any of the compositions of the invention can contain combinations of two or more bioactive agents. It is understood that a biologically active agent can be used in connection with administration to various subjects, for example, to humans (i.e., medical administration) or to animals (i.e., veterinary administration).

As used herein, the term "pharmaceutically active agent" includes a "drug" or a "vaccine" and means a molecule, group of molecules, complex or substance administered to an organism for diagnostic, therapeutic, preventative medical, or veterinary purposes. This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term may also be used in reference to agricultural, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA) or ribonucleic acid (RNA). Pharmaceutically active agents include the herein disclosed categories and specific examples. It is not intended that the category be limited by the specific examples. Those of ordinary skill in the art will recognize also numerous other compounds that fall within the categories and that are useful according to the invention. Examples include a radiosensitizer, the combination of a radiosensitizer and a chemotherapeutic, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifungal agent, a vaccine, a protein, or a nucleic acid. In a further aspect, the pharmaceutically active agent can be coumarin, albumin, bromolidine, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetominophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hydrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides. It is understood that a pharmaceutically active agent can be used in connection with administration to various subjects, for example, to humans (i.e., medical administration) or to animals (i.e., veterinary administration).

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$—$OA^2$ or —$OA^1$—$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

As used herein, the term "peptide amphiphile" refers to a peptide compound possessing both a hydrophilic portion (e.g., a hydrophilic peptide sequence moiety) and a hydrophobic portion (e.g., a hydrocarbon moiety). One property typically associated with a peptide amphiphile can be self-assembly.

As used herein, the term "hydrophilic peptide sequence" refers to a peptide residue sequence having hydrophilicity properties relative to a hydrocarbon moiety. A hydrophilic peptide sequence can comprise one or more functional peptide sequences (e.g., degradable peptide sequences, nitric oxide donors, and/or cell adhesive ligands).

As used herein, the term "degradation sequence" refers to a sequence of peptide residues that can be degraded by enzymes or hydrolysis under biological conditions.

As used herein, the term "cell adhesive sequence" refers to a sequence of peptide residues capable of operation as adhesive ligands for cells. In one aspect, due to amphilic characteristic of peptide amphiphiles, the disclosed cell adhesive sequences are exposed at the exterior surface of a nanofiber assembly; thus, such cell adhesive sequence can be available for interaction with one or more cells. One example is an "endothelial cell adhesive sequence," which refers to a peptide sequence that supports endothelial cell adhesion, spreading, migration, and/or growth.

As used herein, the term "nitric oxide producing donor sequence" refers to a peptide residue (e.g., lysine (K) or cysteine (C)) or sequence of peptide residues (e.g., polylysine (KKKKK) (SEQ ID NO: 3) or polycysteine (CCCCC) (SEQ ID NO: 17)) capable of reversibly binding nitric oxide gas, or equivalent thereof as a complex (e.g., diazoniumdiolates). Thus, the peptide or sequence can serve as a reservoir for nitric oxide gas and can selectively release nitric oxide over time. It is understood that the term can include other nitric oxide doners, for example any peptide sequences containing cystine or amine groups.

As used herein, the term "self-assembling" refers to the characteristic of a plurality of molecules of a compound in which a disordered system forms a more organized structure or pattern as a consequence of specific, local interactions among the molecules themselves, without external direction. In one aspect, peptide amphiphiles can be self-assembling. In a further aspect, a plurality of molecules of a compound can self-assemble into nanofibers. In a yet further aspect, peptide amphiphiles can self-assemble into nanofibers. In a still further aspect, peptide amphiphiles can self-assemble into nanofibers without the need for cross-linking.

B. COMPOSITIONS

Biological compatibility of artificial implants can be improved by mimicking natural systems. Consequently, an ideal stent should have properties similar to the natural endothelium. Thus, disclosed herein is a natural endothelium mimic nanomatrix.

Natural endothelium consists of endothelial cells embedded in a viscoelastic extracellular matrix (ECM). In addition to providing structural integrity, ECM also provides a dynamic, functional environment, which is crucial for cell proliferation, differentiation, and migration (Ross J M. 1998). This concept has inspired the use of ECM-derived cell adhesive ligands for biomimetic scaffolds to control cellular behaviors. Controlling the degradation kinetics of scaffolds is another important factor because the degradation rate affects the ECM production in vitro and tissue formation in vivo (Alsberg E, et al. 2003; Bryant S J, et al. 2002). Cell migration and proliferation are dependent on cell adhesion for many different cell types (Ross J M. 1998). Natural ECM consists of many self-assembled nanostructured fibrillar proteins. Endothelium also serves to maintain the non-thrombogenic environment of the blood vessel by releasing soluble factors like nitric oxide (NO). Therefore, natural endothelium mimicking nanomatrix can be designed to imitate this chemical and biological complexity of the endothelial ECM: 1) endothelial cell adhesive moieties to promote strong endothelial cell retention and migration, 2) cell-mediated degradable sites for endothelial cell migration into the nanomatrix for strong endothelializaiton, 3) self-assembled nanofibrous structure similar to the natural ECM, and 4) release of NO to promote homing of satellite endothelial progenitor cells, along with inhibiting restenosis and thrombosis.

As disclosed herein, a natural endothelium mimic nanomatrix can be produced from peptide amphiphiles comprising a hydrophilic peptide and a hydrophobic tail, wherein the hydrophilic peptide comprises one or more of endothelial cell adhesive moieties to promote strong endothelial cell retention and migration, cell-mediated degradable sites for endothelial cell migration into the nanomatrix for strong endothelializaiton, and release of NO to promote homing of satellite endothelial progenitor cells, along with inhibiting restenosis and thrombosis.

Thus, provided herein is a peptide amphiphile, comprising a hydrophilic peptide sequence and a hydrophobic tail, wherein the hydrophilic peptide sequence comprises a degradation sequence and one or more of a first cell adhesive sequence and a nitric oxide producing donor sequence, wherein the first adhesive sequence is an endothelial cell adhesive sequence that does not bind to smooth muscle cells and/or platelets.

Thus, the hydrophilic peptide sequence can comprise the formula:

DS - - - CA, wherein - - - is a direct or indirect covalent linkage, wherein "DS" is a degradation sequence; and wherein "CA" is an endothelial cell adhesive sequence.

The hydrophilic peptide sequence can comprises the formula:

DS - - - KK, wherein - - - is a direct or indirect covalent linkage, wherein "DS" is a degradation sequence; and wherein "KK" is a nitric oxide producing donor sequence The hydrophilic peptide sequence can comprises the formula:

DS - - - CA - - - KK, wherein - - - is a direct or indirect covalent linkage, wherein "DS" is a degradation sequence; wherein "CA" is an endothelial cell adhesive sequence; and wherein "KK" is a nitric oxide producing donor sequence.

The hydrophilic peptide sequence can comprise the formula:

DS - - - KK - - - CA, wherein - - - is a direct or indirect covalent linkage, wherein "DS" is a degradation sequence; wherein "CA" is an endothelial cell adhesive sequence; and wherein "KK" is a nitric oxide producing donor sequence.

Also disclosed herein is a composition comprising a first and second peptide amphiphile, each independently comprising a hydrophilic peptide sequence and a hydrophobic tail, wherein the hydrophilic peptide sequence of the first peptide amphiphile comprises a degradation sequence and an endothelial cell adhesive sequence, and wherein the hydrophilic peptide sequence of the second peptide amphiphile comprises a degradation sequence and a nitric oxide producing donor sequence.

Thus, the hydrophilic peptide sequence of the first peptide amphiphile can comprise the formula:

DS - - - CA, wherein each - - - is independently a direct or indirect covalent linkage, wherein "DS" is a degradation sequence; and wherein "CA" is an endothelial cell adhesive sequence; and the hydrophilic peptide sequence of the second peptide amphiphile can comprise the formula:

DS - - - KK, wherein "KK" is a nitric oxide producing donor sequence.

The first and second peptide amphiphiles can be present in the disclosed composition at a ratio of from about 1:20 to about 20:1, including about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. Thus, the first and second peptide amphiphiles can be present in the composition at a ratio of from about 1:9 to about 9:1.

The herein disclosed compositions can further comprise one or more additional peptide amphiphiles comprising a degradation sequence but not comprising either a endothelial cell adhesive sequence or nitric oxide producing donor sequence. These one or more additional peptide amphiphiles can comprise additional functional moieties. These one or more additional peptide amphiphiles can comprise non-functional sequences. The skilled artisan can use these additional peptide amphiphiles to control the concentration of the first and second peptide amphiphiles. For example, wherein the first and second peptide amphiphiles are present in the composition at a ratio of about 9:1, the can also be present in the composition with a third peptide amphiphile at a ratio of, for example, about 9:1:0.1, 9:1:0.2, 9:1:0.3, 9:1:0.4, 9:1:0.5, 9:1:0.6, 9:1:0.7, 9:1:0.8, 9:1:0.9, 9:1:1, 9:1:2, 9:1:3, 9:1:4, 9:1:5, 9:1:6, 9:1:7, 9:1:8, 9:1:9, 9:1:10. Many other such combinations and mixtures can be selected by the skilled artisan and tested for optimal performance using routine skill.

1. Peptide Amphiphile

A peptide amphiphile (PA) is an amphiphilic structure typically with a short hydrophilic peptide sequence conjugated with a single hydrophobic tail (Paramonov S E, et al. 2006). Depending on their shape, charge, and environment these molecules can self-assemble into sheets, spheres, rods, disks, or channels (Lowik D, et al. 2004). Amphiphiles with a conical shape, such that the hydrophilic head group is bulkier than the hydrophobic tail, are known to form cylindrical micelles (Jun H W, et al. 2006). Amphiphilic nature of the PAs is responsible for their self-assembly. In a neutral solution, the negatively charged amino acids in the backbone of the PAs can help to solubilize it. In order to induce self-assembly, the repelling forces due to presence of negative charges can be eliminated. This can be achieved by lowering the pH of the PA solution or addition of divalent ions (Hartgerink J D, et al. 2002; Hartgerink J D, et al. 2001; Jun H W, et al. 2005). In a self-assembled nanofiber structure, the four amino acids closest to the core can form hydrogen bonds. The presence or absence of these hydrogen bonds can define the cylindrical or the spherical orientation of the self-assembled structure (Paramonov S E, et al. 2006).

Amphiphilicity is widely found in natural biological systems, such as cell membranes. It is the major driving force responsible for the self-assembly of biomolecules into supramolecular structures with complex hierarchical order. This concept indicates the use of PAs for biomimetic scaffolds (Curtis A, et al. 2001; Barnes C P, et al. 2007). PAs consisting of various bioactive sequences, like cell adhesive ligands or biodegradable sequences, can be self-assembled under physiological conditions to form supramolecular structures similar to the naturally occurring biomolecules. Recently, they have been extensively studied for various biomedical applications including growth of blood vessels (Malkar N B, et al. 2003; Hosseinkhani H, et al. 2006; Rajangam K, et al. 2006) and bone tissue repair (Hosseinkhani H, et al. 2007; Hosseinkhani H, et al. 2006; Sargeant T D, et al. 2008).

PAs are attractive templates for biomimetic scaffolds because of the ease of incorporating different cell adhesion and degradation moieties in their backbone (Jun H W, et al. 2006; Jun H W, et al. 2005).

The herein disclosed peptide amphiphile can in some aspects be any modified peptide capable of self-assembling into a nanomatrix. In some aspects, the disclosed peptide amphiphile comprises a hydrophilic peptide and a hydrophobic tail. The length of the hydrophilic peptide and hydrophobic tail can be selected such that the peptide amphiphile maintains the ability to self-assemble into a nanomatrix. Thus, for example, the length of the hydrophobic tail can be increased to accommodate for an increased length in the hydrophilic peptide. The skilled artisan can use routine skill to screen for the ability of a peptide amphiphile with a selected hydrophilic peptide and a selected hydrophobic tail to self-assemble into a nanomatrix.

2. Nitric Oxide (NO)

NO released from the endothelium is known to block a number of key events in the restenosis cascade. NO plays a pivotal role in regulating vessel wall homeostasis (Marin J, et al. 1997; Kuo P C, et al. 1995; Davies K M, et al. 2001). It is continuously released from amino acid L-arginine in healthy endothelial cells by the enzyme, nitric oxide synthase. NO released from the endothelium stimulates soluble guanylyl cyclase, increasing concentrations of cyclic guanosine monophosphate (GMP)(Kuo P C, et al. 1995). The increase of cyclic GMP levels in vascular smooth muscle cells underlying the endothelium leads to activation of GMP-dependent kinases that decrease intracellular calcium, resulting in relaxation of smooth muscle cells (SMCs). Local relaxation of SMCs in response to sudden constriction of a blood vessel is critical for maintaining laminar blood flow (Beckman J S. 1996). NO released into the blood vessel lumen increases cyclic GMP levels in platelets as well. It decreases platelet activation and adhesion to the surface of the endothelium, rendering the vascular wall non-thrombogenic. NO regulates the cellular environment within the blood vessel by inhibiting the activity of growth factors released from the platelets (Kuo P C, et al. 1995). Given its antithrombogenic role, the incorporation of NO is expected to improve the biological properties of vascular prostheses. NO-releasing polymers have been successfully developed such as poly(vinyl chloride), silicone rubber, polymethacrylate, and polyurethane for uses as non-thrombogenic coatings for cardiovascular devices (Reynolds M M, et al. 2004; Verma S, et al. 2005). For example, NO has been successfully incorporated into vascular grafts in the form of diazeniumdiolates (a special class of compound capable of releasing NO in blood) (Pulfer S K, et al. 1997). Initial studies in rabbits show that controlled release of NO from NO-containing microspheres loaded in channeled stents limited in-stent restenosis (Do Y, et al. 2004). In another 28 day study, stent-based nitric oxide delivery from sodium nitroprusside has been investigated in porcine models and shown to reduce neointimal proliferation (Hou D, et al. 2005). In addition to the aforementioned functions, NO is also known for its ability to promote endothelial cell growth, survival and migration (Ziche M, et al. 1994; Kawasaki K, et al. 2003). NO also plays a critical role in neovascularization partly by recruitment of circulating endothelial progenitor cells (Aicher A, et al. 2003). To this effect, local delivery of NO from hydrogels has been shown to enhance the rate of vessel re-endothelialization (Lipke E A, et al. 2005).

The antithrombogenic, homeostatic and pro-endothelialization properties of NO make it an attractive candidate as a therapeutic drug coating on stents. However, the short half-life of only a few seconds in vivo makes NO unsuitable for direct administration as a systemic drug (Miller M, et al. 2007). Also, NO gas is difficult to handle due to the necessity of complete oxygen exclusion, which is needed to prevent its oxidation. Hence, NO carriers are used to stabilize it until the time of release (Hanson S R, et al. 1995; Miller M, et al. 2007). Currently, two types of NO donor drugs are clinically used: (1) organic nitrates and (2) sodium nitroprusside (Miller M, et al. 2007). Nitroglycerine is a clinically used organic nitrate. It is used in transdermal patches for the treatment of heart failure and chronic angina. Nitroglycerine contains three nitroxy-ester (nitrite) groups, which undergo enzyme-mediated release. The major limiting factor of this drug is the development of tolerance after prolonged continuous use. Sodium nitroprusside is used on-site in hospitals to reduce blood pressure in hypersensitive crises. It contains an iron molecule coordinated to five cyanide molecules and one molecule of NO. The NO molecule is rapidly released during infusion, whereas the cyanide molecules are liberated gradually. These cyanide molecules can reach toxic levels in some cases, presenting a major limitation to the use of this drug (Gori T, et al. 2002).

Disclosed herein is a class of NO-releasing compound called diazeniumdiolates, also known as NONOates. The chemical structure of these compounds can be inferred from the name: diazen N═N, ium: formal positive charge, diolate: two negative oxygens (Paramonov S E, et al. 2006; Saavedra J, et al. 2000).

The following is the chemical structure of a diazeniumdiolate:

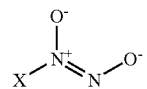

Diazeniumdiolates can be formed by the reaction of a nucleophilic amine (X—) with NO as shown in the following reaction:

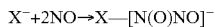

Diazoniumdiolates then dissociate on protonation to release free NO as shown in the following reaction:

Owing to its electron acceptor properties, NO can react with nucleophilic amines to form diazoniumdiolates. When dissolved in buffer, blood, or cell culture medium, the diazeniumdiolates undergo protonation and disassociation to release NO (Saavedra J, et al. 2000; Keefer L K, et al. 1996; Hrabie J A, et al. 2002). The release kinetics can be controlled by the structure of the nucleophilic amines. Diazeniumdiolates can be synthesized by direct reaction with amines under high pressure in the absence of air.

Other nitric oxide-releasing diazeniumdiolate compounds are known in the art. For example, nitrogen- and carbon-based NO donor complexes are available in the art with half-lives at physiological pH ranging from a few seconds to many days.

The most common diazeniumdiolates are formed by the reaction of secondary amines and polyamines with nitric oxide in basic media. These are stable solids, capable of regenerating 2 equivalents of nitric oxide and the starting amine in neutral or acidic buffers. The half-life of NO generation varies from a few seconds to many hours depending on the amine. The decomposition to NO is a spontaneous, first-order reaction at constant pH. An example of an underivatized diazeniumdiolate:

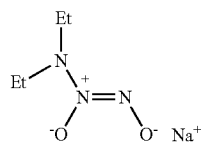

i. O-Derivatized Diazeniumdiolates

The diazeniumdiolate anions react with electrophiles to produce stable covalent compounds. These compounds have the ability to act as prodrugs, releasing nitric oxide only when metabolically converted to the diazeniumdiolate anion. Several compounds of this class have been synthesized by reaction of alkyl or aryl halides, sulfate esters, epoxides, etc. with the ionic diazeniumdiolates. Examples of O-derivatized diazeniumdiolates:

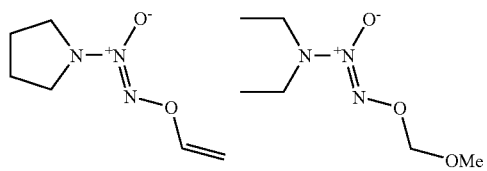

ii. C-Based Diazeniumdiolates

Compounds containing the diazeniumdiolate group bound to carbon have been known for over 100 years under names such as "isonitramines", and "nitrosohydroxylamines" even though these are not accurate descriptions of the bonding as shown by numerous X-ray structural determinations. While attachment to a carbon obviously presents great advantages of flexibility for the design of new NO donors, it must be recognized that not all of these materials produce NO spontaneously. The range of reactivity of these compounds runs the full scale from materials which are so stable that no NO is ever produced (rare) to those which decompose violently (also rare). Many also produce mixtures of NO and $N_2O$ rather than pure NO. Examples of C-based diazeniumdiolates:

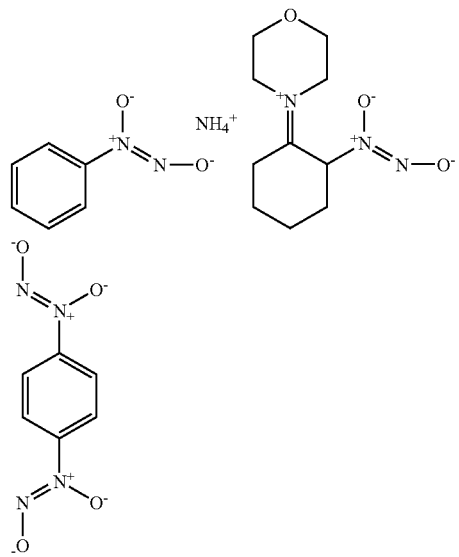

iii. Polymer-Based Diazeniumdiolates

To modulate the time course of NO release and also limit NO exposure to selected sites of the body, the diazeniumdiolate functional group can be incorporated into polymeric matrices. The NO-releasing polymers range from films, microspheres and gels to powders and moldable resins. Polymeric diazeniumdiolates have been shown to improve thromboresistivity in intra-arterial devices and can serve as important tools in cardiovascular research. Example of a polymer-based diazeniumdiolate:

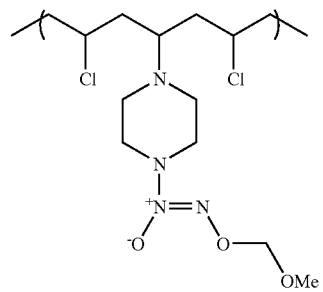

iv. Lysine

Preferrably, the nucleophilic amine is on the side chain (R group) of an amino acid (natural or artificial). For example, the nucleophilic amine can be on the side chain (R group) of lysine. As shown below, lysine has two pendant amine groups for NO binding.

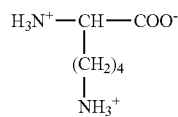

Controlled release of NO from lysine-based polymers has been shown to reduce platelet attachment and smooth muscle cell proliferation, which are major causes of restenosis (Jun H, et al. 2005; Bohl K S, et al. 2000; Jun H W, et al. 2005). The lysine residues can have pendant amine groups that react with NO to form a diazeniumdiolate-modified peptide [K[N(O)NO⁻]]$_n$.

Thus, the nitric oxide producing donor sequence can comprise one or more diazeniumdiolate-modified lysine residues. Thus, the nitric oxide producing donor sequence can comprise the diazeniumdiolate-modified amino peptide [K[N(O)NO⁻]]$_n$, wherein "n" is from 1 to 20. In some aspects, n is 1, 2, 3, 4, 5, 6, 7, 8, 9, 10, 11, 12, 13, 14, 15, 16, 17, 18, 19, 20 or higher. Thus, the nitric oxide producing donor sequence can comprise the diazeniumdiolate-modified peptide [K[N(O)NO⁻]]$_5$.

The nitric oxide producing donor sequence can comprise one or more lysine residues comprising pendant amine groups that react with NO to form a diazeniumdiolate-modified peptide. Thus, the nitric oxide producing donor sequence can comprise the amino acid sequence Lys-Lys-Lys-Lys-Lys (SEQ ID NO:3), wherein one or more of the lysine residues comprise pendant amine groups that react with NO to form a diazeniumdiolate-modified peptide.

The nitric oxide producing donor sequence can comprise one or more cysteine residues comprising pendant thiol groups that react with NO to form a modified peptide. Thus, the nitric oxide producing donor sequence can comprise the amino acid sequence Cys-Cys-Cys-Cys-Cys (SEQ ID NO:17), wherein one or more of the cysteine residues comprise pendant thiol groups that react with NO to form a modified peptide.

It is understood that each lysine residue can be a donor for two nitric oxide molecules. The number of lysine residues or diazeniumdiolate-modified lysine residues can therefore be selected based on the amount of NO desired. This can further be regulated by the artisan by selecting the amount or concentration of the peptide amphiphiles comprising these lysine residues. For example, disclosed herein is an endothelial mimicking matrix comprising a first PA comprising an endothelial cell adhesion sequence YIGSR (SEQ ID NO: 2) ("PA-YIGSR") and a second PA comprising a NO donor sequence KKKKK (SEQ ID NO: 3) ("PA-KKKKK") at a ratio of 9:1, wherein KKKKK (SEQ ID NO: 3) comprises five diazeniumdiolate-modified lysine residues. The skilled artisan could therefore achieve the same result by increasing the number of diazeniumdiolate-modified lysine residues in the second peptide amphiphile and comcomitantly increasing the ratio of the first PA to second PA (>9:1).

3. EC Adhesion

Retention of endothelial cells in the lumen of DES is critical to its performance. Endothelialization results in a non-thrombogenic coating to the exposed stent surface, the absence of which leaves the stent struts in direct contact with flowing blood and eventual thrombus formation. Laminin is the major non-collagenous glycoprotein component of basement membranes and is a mediator of cell adhesion, migration, growth, and differentiation (Beck K, et al. 1990). YIGSR (SEQ ID NO: 2) is a laminin-derived cell adhesive sequence, known to enhance attachment, spreading, and migration of endothelial cells (Hubbell J A, et al. 1991). Cell spreading via YIGSR (SEQ ID NO: 2) is mediated by a 67-kDa cell membrane associated receptor (Massia S P, et al. 1993). Use of YIGSR (SEQ ID NO: 2) for modification of surfaces like polyethylene terephthalate and polytetrafluoroethylene was shown to selective enhance EC adhesion, spreading, migration (Massia S P, et al. 1991; Fittkau M H, et al. 2005) and promote EC colony formation.

The incorporation of YIGSR (SEQ ID NO: 2) sequence in polyurethane has shown to enhance endothelial cell adhesion and spreading (Jun H, et al. 2004). NO releasing polyurethanes were developed by incorporating lysine-based diazeniumdiolates in the polymer (Jun H W, et al. 2005). This polymer has been shown to dramatically decrease platelet adhesion and inhibit smooth muscle cell proliferation, while stimulating endothelial cell adhesion. Furthermore, it has been observed that the incorporation of YIGSR (SEQ ID NO: 2) sequence into the NO releasing polymer backbone enhances endothelial cell proliferation while at the same time inhibiting platelet attachment (Taite L J, et al. 2008).

The disclosed hydrophilic peptide can therefore comprise a first adhesive sequence that selectively binds endothelial cells and thus selectively promotes the binding of endothelial cells to a nanomatrix comprising the disclosed peptide amphiphiles. Thus, the disclosed hydrophilic peptide can comprise a first adhesive sequence comprising an endothelial cell adhesive sequence that binds to endothelial cells but does not substantially bind to smooth muscle cells and/or platelets. Thus, the endothelial cell adhesive sequence of the disclosed hydrophilic peptide can comprise the amino acid sequence Tyr-Ile-Gly-Ser-Arg (YIGSR; SEQ ID NO:2).

The hydrophilic peptide of the disclosed peptide amphiphile can further comprise one more additional cell adhesive sequences. In some aspects, the one more additional cell adhesive sequences bind endothelial cells and thus promote the binding of endothelial cells to a nanomatrix comprising the disclosed peptide amphiphiles. Thus, the one more additional cell adhesive sequences can be one or more of Arg-Gly-Asp (SEQ ID NO:8), Arg-Gly-Asp-Ser (SEQ ID NO:9), Asp-Gly-Glu-Ala (SEQ ID NO:10), Val-Ala-Pro-Gly (SEQ ID NO:11), Arg-Glu-Asp-Val (SEQ ID NO:12), Asp-Gly-Glu-Ala (SEQ ID NO:13), and Lys-Arg-Ser-Arg (SEQ ID NO:14). Other such cell adhesive sequences, including endothelial cell adhesive sequences (selective and non-selective) are known and can be used in the disclosed peptide amphiphiles. The skilled artisan can screen peptide amphiphiles comprising candidate cell adhesive sequences using routine in vitro methods.

4. Degradation Sequence

The degradation sequence can comprise an amino acid sequence that undergoes cell-mediated proteolytic degradation.

In some aspects, the degradation sequence comprises a matrix metalloprotease (MMP) specific cleavage site. (MMPs are zinc-dependent endopeptidases belonging to a larger family of proteases known as the metzincin superfamily.

The most commonly used groupings of MMPs are based partly on historical assessment of the substrate specificity of the MMP and partly on the cellular localisation of the MMP. These groups are the collagenases, the gelatinases, the stromelysins, and the membrane type MMPs (MT-MMPs).

The collagenases are capable of degrading triple-helical fibrillar collagens into distinctive ¾ and ¼ fragments. These collagens are the major components of bone and cartilage, and MMPs are the only known mammalian enzymes capable of degrading them. Traditionally, the collagenases are MMP1, MMP8, MMP13, and MMP18. In addition, MMP14 has also been shown to cleave fibrillar collagen, and more controversially there is evidence that MMP2 is capable of collagenolysis.

The main substrates of the gelatinases are type IV collagen and gelatin, and these enzymes are distinguished by the presence of an additional domain inserted into the catalytic domain. This gelatin-binding region is positioned immediately before the zinc binding motif, and forms a separate folding unit which does not disrupt the structure of the catalytic domain. The gelatinases are MMP2 and MMP9.

The stromelysins display a broad ability to cleave extracellular matrix proteins but are unable to cleave the triple-helical fibrillar collagens. The three canonical members of this group are MMP3, MMP10, and MMP11.

All six membrane type MMPs (MMP14, MMP15, MMP16, MMP17, MMP24, and MMP25) have a furin cleavage site in the pro-peptide, which is a feature also shared by MMP11.

Examples of additional MMP cleavage sites are known and described, for example, in Handbook of proteolytic enzymes, Edited by Alan J. Barrett, Neil D. Rawlings, J. Fred Woessner, Academic Press.

TABLE 1

MMPs

| MMP | Group | Cleavage Site | SEQ ID NO: |
|---|---|---|---|
| MMP1 | collagenases | GPQGIWGQ | SEQ ID NO: 16 |
| MMP2 | gelatinases | GTAGLIGQ or | SEQ ID NO: 1 |
| | | GPQGLLGA | SEQ ID NO: 15 |

Thus, the degradation sequence comprises a matrix metalloprotease-2 (MMP2) specific cleavage site. For example, the degradation sequence can comprise the amino acid sequence Gly-Thr-Ala-Gly-Leu-Ile-Gly-Gln (SEQ ID NO: 1)

Incorporation of an MMP specific sequence, such as an MMP-2 specific sequence, in the PA backbone can ensure that the nanomatrix undergoes cell-mediated proteolytic degradation, enabling cell migration through the nanomatrix and eventual remodeling with natural ECM (Jun H W, et al. 2005; Giannelli G, et al. 1997). For MMP2, this cleavage is expected between glycine and leucine residues (Jun H W, et al. 2005).

5. Hydrophobic Tail

The hydrophobic tail can comprise a moiety having an optionally substituted C4 or larger alkyl chain. Thus, the hydrophobic tail can comprise a moiety having an optionally substituted C6 to C28 or larger alkyl chain. Thus, the hydrophobic tail can comprise a moiety having an optionally substituted C10 to C25 or larger alkyl chain. Thus, the hydrophobic tail can comprise a moiety having an optionally substituted C5, C5, C6, C7, C8, C9, C10, C11, C12, C13, C14, C15, C16, C17, C18, C19, C20, C21, C22, C23, C24, C25, C26, C27, C28, or larger alkyl chain. Thus, the hydrophobic tail can comprise a moiety having an optionally substituted C16 alkyl chain.

6. Specific Embodiments

The hydrophilic peptide sequence can comprise the amino acid sequence Gly-Thr-Ala-Gly-Leu-Ile-Gly-Gln (SEQ ID NO:1) and the amino acid sequence Tyr-Ile-Gly-Ser-Arg (SEQ ID NO:2). Thus, the hydrophilic peptide sequence can comprise the amino acid sequence Gly-Thr-Ala-Gly-Leu-Ile-Gly-Gln-Tyr-Ile-Gly-Ser-Arg (SEQ ID NO:4).

The hydrophilic peptide sequence can comprise the amino acid sequence Gly-Thr-Ala-Gly-Leu-Ile-Gly-Gln (SEQ ID NO:1) and the amino acid sequence Lys-Lys-Lys-Lys-Lys (SEQ ID NO:3), wherein the lysine residues comprises pendant amine groups that react with NO to form a diazeniumdiolate-modified peptide. Thus, the hydrophilic peptide sequence can comprise the amino acid sequence Gly-Thr-Ala-Gly-Leu-Ile-Gly-Gln-Lys-Lys-Lys-Lys-Lys (SEQ ID NO:5), wherein the lysine residues comprises pendant amine groups that react with NO to form a diazeniumdiolate-modified peptide.

The hydrophilic peptide sequence can comprise the amino acid sequence Gly-Thr-Ala-Gly-Leu-Ile-Gly-Gln (SEQ ID NO:1), the amino acid sequence Tyr-Ile-Gly-Ser-Arg (SEQ ID NO:2), and amino acid sequence Lys-Lys-Lys-Lys-Lys (SEQ ID NO:3), wherein the lysine residues comprises pendant amine groups that react with NO to form a diazeniumdiolate-modified peptide. Thus, the hydrophilic peptide sequence can comprise the hydrophilic peptide sequence comprises the amino acid sequence Gly-Thr-Ala-Gly-Leu-Ile-Gly-Gln-Tyr-Ile-Gly-Ser-Arg-Lys-Lys-Lys-Lys-Lys (SEQ ID NO:6), wherein the lysine residues comprises pendant amine groups that react with NO to form a diazeniumdiolate-modified peptide. Thus, the hydrophilic peptide sequence can comprise the amino acid sequence Gly-Thr-Ala-Gly-Leu-Ile-Gly-Gln-Lys-Lys-Lys-Lys-Lys-Tyr-Ile-Gly-Ser-Arg (SEQ ID NO:7), wherein the lysine residues comprises pendant amine groups that react with NO to form a diazeniumdiolate-modified peptide.

7. ECM Mimicking Nanomatrix

Disclosed herein is an endothelium mimicking nanomatrix, comprising one or more of the herein disclosed peptide amphiphiles assembled into nanofibers. The nanofibers can comprise a mixture of peptide amphiphiles having formulas DS - - - CA and DS - - - KK.

The DS - - - CA and DS - - - KK peptide amphiphiles can be present in the nanofibers at a ratio of from about 1:20 to about 20:1, including about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. Thus, the nanofibers can comprise a mixture of peptide amphiphiles having formulas DS - - - CA and DS - - - KK. The DS - - - CA and DS - - - KK peptide amphiphiles can be present in the nanofibers at a ratio of from about 1:9 to about 9:1. As disclosed herein, this ratio can be selected by the skilled artisan based in part on the number of diazeniumdiolate-modified lysine residues in the one or more peptide amphiphiles and the desired NO release.

The DS - - - CA peptide amphiphile of the disclosed endothelium mimicking nanomatrix can comprise the amino acid sequence Gly-Thr-Ala-Gly-Leu-Ile-Gly-Gln (SEQ ID NO:1) and the amino acid sequence Tyr-Ile-Gly-Ser-Arg (SEQ ID NO:2). Thus, the DS - - - CA peptide amphiphile of the disclosed endothelium mimicking nanomatrix can comprise the amino acid sequence Gly-Thr-Ala-Gly-Leu-Ile-Gly-Gln-Tyr-Ile-Gly-Ser-Arg (SEQ ID NO:4).

The DS - - - KK peptide amphiphile of the disclosed endothelium mimicking nanomatrix can comprise the amino acid sequence Gly-Thr-Ala-Gly-Leu-Ile-Gly-Gln (SEQ ID NO:1) and one or more lysine residues comprising pendant amine groups that can react with nitric oxide to form a diazeniumdiolate-modified peptide. Thus, the DS - - - KK peptide amphiphile of the disclosed endothelium mimicking nanomatrix can comprise the amino acid sequence Gly-Thr-Ala-Gly-Leu-Ile-Gly-Gln (SEQ ID NO:1) and the amino acid sequence Lys-Lys-Lys-Lys-Lys (SEQ ID NO:3), wherein the lysine residues comprises pendant amine groups that react with nitric oxide to form a diazeniumdiolate-modified peptide. Thus, the DS - - - KK peptide amphiphile of the disclosed endothelium mimicking nanomatrix can comprise the amino acid sequence Gly-Thr-Ala-Gly-Leu-Ile-Gly-Gln-Lys-Lys-Lys-Lys-Lys (SEQ ID NO:5), wherein the lysine residues comprises pendant amine groups that react with NO to form a diazeniumdiolate-modified peptide. In some aspects, the DS - - - KK peptide amphiphile has reacted with nitric oxide to form a diazeniumdiolate-modified peptide $[K[N(O)NO^-]]_n$. In some aspects, n can be from 1 to 20. In some aspects, n is 1, 2, 3, 4, 5, 6, 7, 8, 9, 10, 11, 12, 13, 14, 15, 16, 17, 18, 19, 20 or higher. In some aspects, the DS - - - KK peptide amphiphile has reacted with nitric oxide to form a diazeniumdiolate-modified peptide $[K[N(O)NO^-]]_5$.

The nanofibers of the disclosed endothelium mimicking nanomatrix can comprise peptide amphiphiles having the formula DS - - - CA - - - KK, DS - - - KK - - - CA, or a combination thereof. For example, the DS - - - CA - - - KK and DS - - - KK - - - CA peptide amphiphiles can comprise the amino acid sequence Gly-Thr-Ala-Gly-Leu-Ile-Gly-Gln (SEQ ID NO:1), the amino acid sequence Tyr-Ile-Gly-Ser-Arg (SEQ ID NO:2), and the amino acid sequence Lys-Lys-Lys-Lys-Lys (SEQ ID NO:3), wherein the lysine residues comprises pendant amine groups that react with NO to form a diazeniumdiolate-modified peptide. For example, the DS - - - CA - - - KK peptide amphiphile can comprise the amino acid sequence Gly-Thr-Ala-Gly-Leu-Ile-Gly-Gln-Tyr-Ile-Gly-Ser-Arg-Lys-Lys-Lys-Lys-Lys (SEQ ID NO:6), wherein the lysine residues comprises pendant amine groups that react with NO to form a diazeniumdiolate-modified peptide. The DS - - - KK - - - CA peptide amphiphile can comprise the amino acid sequence Gly-Thr-Ala-Gly-Leu-Ile-Gly-Gln-Lys-Lys-Lys-Lys-Lys-Tyr-Ile-Gly-Ser-Arg (SEQ ID NO:7), wherein the lysine residues comprises pendant amine groups that react with NO to form a diazeniumdiolate-modified peptide.

In some aspects, the peptide amphiphile of the disclosed endothelium mimicking nanomatrix has reacted with nitric oxide to form a diazeniumdiolate-modified peptide $[K[N(O)NO^-]]_n$. In some aspects, n is from 1 to 20. In some aspects, n is 1, 2, 3, 4, 5, 6, 7, 8, 9, 10, 11, 12, 13, 14, 15, 16, 17, 18, 19, 20 or higher. Thus, in some aspects, the peptide amphiphile has reacted with nitric oxide to form a diazeniumdiolate-modified peptide $[K[N(O)NO^-]]_5$.

8. Stents

Also disclosed herein is a composition comprising a medical device coated with an endothelium mimicking nanomatrix disclosed herein. The medical device can be any device known or identified for use inside the body of a subject. Preferably, the medical device is one that is inserted into the cardiovascular system. The medical device can comprise any material suitable for use as a surgical implant.

Most stents are crafted from 316L stainless steel. Current examples include the Cordis Palmaz-Schatz stent, the Cordis Crossflex stent, the Guidant MultiLink stent, and the Medtronic Bestent. Disadvantages of steel stents include the high occurrence of subacute thrombosis and restenosis, bleeding complications, corrosion, and re-dilation of the stented vessel segment.

Gold has long been known as a highly visible, biocompatible, and usually inert metal. Gold-plated hybrid stents exhibit good visibility and flexibility, but are also quite expensive.

Currently, CONICHROME®, PHYNOX™ and ELGILOY® are trademark names for the cobalt-chromium-nickel-molybdenum-iron alloy. This cobalt chromium alloy can be used for manufacturing stents like the Schneider Wallstent.

Tantalum, element #73, is a shiny, flexible, and highly radio-opaque metal. Though more brittle than stainless steel, tantalum exhibits high ductility and resistance to corrosion. Current examples of tantalum stents include the Wiktor Stent by Medtronic and the Tantalum Cordis Stent.

Nitinol (from the "Nickel Titanium Naval Ordinance Laboratory") is an example of a biocompatible, super-elastic shape-memory alloy. As a shape-memory alloy consisting of 55% nickel and 45% titanium, nitinol has the ability to return to a specific shape upon heating to a certain temperature after its phase transition. Shape-memory alloys undergo a phase transition in their crystal structure when cooled from their stronger, higher temperature form in the Austenitic phase to their weaker, lower temperature form in the Martensitic phase. Nitinol also has a springy, "rubber-like" behavior that allows it to be super-elastic and contorted at its austenitic temperature. The strong intermetallic bond between nickel and titanium has a very low reaction rate, even in patients with increased sensitivity to nickel. This prevents a strong immunological response and decreases corrosion. Present examples include Boston Scientific's Nitinol-self-expanding Radius stent. Boston Scientific's Symbiot stent, available in Europe, is comprised of nitinol covered on both sides by 16-micron thick layers of ePTFE.

Materials for polymer stents include biodegradable stents coupled with polymeric endoluminal paving, and shape-memory polymers. Silicone was the first organic material chosen for stenting. Silicone is a condensation polymer derived from alternating silicone and oxygen atoms which induces low rates of tissue trauma. However, silicone has poor biodurability, tensile and coil strength, and inner to outer diameter ratio.

Pure plastic biliary stents using polyethylene or polyurethane have also been used in patients. However, polyethylene induces sludge in 20-30% of patients, encourages protein adherence and biofilm formation, and entraps bile crystals and food particles. In contrast, polyurethane has good tensile and coil strength, and good biodurability, but it is also one of the most reactive materials available.

Biodegradable and bioabsorbable stents are also viable materials for stenting. Though biodegradation, bioabsorption, and bioerosion are often used incorrectly as synonyms, they have different definitions. In biodegradation, a biological agent like an enzyme or a microbe is the dominant component in the degradation process. Biodegradable implants are usually useful for short-term or temporary applications. Bioresorption and bioabsorption imply that the degradation products are removed by cellular activity, such as phagocytosis, in a biological environment. By contrast, a bioerodible polymer is a water-insoluble polymer that has been converted under physiological conditions into water-soluble materials. This occurs regardless of the physical mechanism involved in the erosion process. The prefix "bio" in this case refers to erosion occurring in physiological conditions, as opposed to erosion via high temperature, strong acids or bases, or weather.

Because of a stent's temporary structural support to damaged blood vessels, biodegradable polymers can be viewed as a biocompatible, yet easily disposable material, perfect for drug delivery systems. Some biodegradable polymers, such as polyesters, polyorthoesters, and polyanhydrides, may be able to modulate the local delivery of drugs and also degrade "safely" via hydrolytic and other mechanisms. Biodegradable drug delivery systems require steady degradation, permeability, and moderate tensile strength. In a stent, structural support must be accompanied by biocompatibility, hemocompatibility, and good hemodynamics. Currently, biodegradable stents usually induce thrombosis and vascular injury.

The Duke Bioabsorbable Stent was the first biodegradable stent. Others have also tried incorporating natural polymers by forming Type I collagen from purified bovine Achilles' tendons into a tube without slotted sides which was chemically cross-linked for structural stability. Collagen is quite hemocompatible because it carries an inherently negative charge. Collagen products are biocompatible throughout their lifecycle, and have shown a decrease in thromobosis. Also, anticoagulants and fibrinolytic agents can be bound directly to collagen, which aids in its capacity for drug delivery. Cordis Corporation has also developed a biodegradable stent prototype crafted from a blend of polylactide and trimethylene carbonate.

Some factors that accelerate polymer degradation include providing the product with a more hydrophilic backbone, more hydrophilic endgroups, less crystallinity, more porosity, and a smaller overall size. The most common chemical functional groups used are esters, anhydrides, orthoesters, and amides.

A final polymeric possibility is shape-memory polymers. Once the polymer is synthesized, it can be heated or cooled into myriad shapes. Upon introducing a suitable stimulus, the polymer will transition from its temporary state to a memorized, permanent shape. Most of these polymers are created from suitable segments, primarily determined by screening the qualities of existing aliphatic polyesters, especially poly (etherester)s, as well as L,L-dilactide, diglycolid, and p-dioxanone. Macrodiols can be synthesized based on these already-approved monomers.

Thus, the herein disclosed medical device, such as stent, can comprise titanium alloy. The medical device can comprise cobalt-cromium. The medical device can comprise nickle-titanium. The medical device can comprise a biodegradable polymer.

In some aspects, the medical device is a vascular stent. In some aspects, the stent is a drug eluting stent. For example, the stent can be a sirolimus-eluting stent or a paclitaxel-eluting stent.

The skilled artisan can appreciate additional medical devices for use with the disclosed endothelium mimicking nanomatrix. Preferably, the medical device is one administered to a tissue or organ of the body normally comprising a natural endothelium. For example, in some aspects, the medical device is a vascular graft. In some aspects, the medical device is a catheter. In some aspects, the medical device is a pacemaker. In some aspects, the medical device is a heart valve.

Also disclosed are methods of implanting the disclosed coated medical devices into a subject. Thus, in one aspect, a method comprises the steps of providing a composition comprising a medical device (e.g., stent, vascular graft, catheter, pacemaker, or heart valve) coated with an endothelium mimicking nanomatrix and implanting the coated substrate into a subject. In a further aspect, providing is coating a medical device with an endothelium mimicking nanomatrix. In a further aspect, a method comprises the step of coating an endothelium mimicking nanomatrix onto a medical device before implantation into a subject. In a further aspect, a method comprises the step of coating an endothelium mimicking nanomatrix onto a medical device after implantation into a subject.

9. Peptides

As discussed herein there are numerous variants of the functional peptides/proteins that are known and herein contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Table 2 and are referred to as conservative substitutions.

TABLE 2

Amino Acid Substitutions
Original Residue Exemplary Conservative
Substitutions, others are known in the art.

| Original | Substitution |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |

TABLE 2-continued

Amino Acid Substitutions
Original Residue Exemplary Conservative
Substitutions, others are known in the art.

| | |
|---|---|
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another or replacing one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, can be accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent than natural amino acids. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14 (10): 400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH═CH— (cis and trans), —$COCH_2$—, —CH(OH)$CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH$_2$NH—, CH$_2$CH$_2$—); Spatola et al. Life Sci 38:1243-1249 (1986) (—CHH$_2$—S); Hann J. Chem. Soc Perkin Trans. I 307-314 (1982) (—CH═CH—, cis and trans); Almquist et al. J. Med. Chem. 23:1392-1398 (1980) (—COCH$_2$—); Jennings-White et al. Tetrahedron Lett 23:2533 (1982) (—COCH$_2$—); Szelke et al. European Appln, EP 45665 CA (1982): 97:39405 (1982) (—CH(OH)CH$_2$—); Holladay et al. Tetrahedron. Lett 24:4401-4404 (1983) (—C(OH)CH$_2$—); and Hruby Life Sci 31:189-199 (1982) (—CH$_2$—S—); each of which is incorporated herein by reference. A particularly preferred non-peptide linkage is —CH$_2$NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

10. Nucleic Acids

There are a variety of molecules disclosed herein that are nucleic acid based, including for example the nucleic acids that encode, for example, the peptide amphiphiles disclosed herein. The disclosed nucleic acids can be made up of for example, nucleotides, nucleotide analogs, or nucleotide substitutes. Non-limiting examples of these and other molecules are discussed herein. It is understood that for example, when a vector is expressed in a cell, the expressed mRNA will typically be made up of A, C, G, and U. Likewise, it is understood that if, for example, an antisense molecule is introduced into a cell or cell environment through, for example exogenous delivery, it is advantageous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to the base, the sugar, and/or the phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

There are a variety of sequences related to the protein molecules involved in the signaling pathways disclosed herein, all of which are encoded by nucleic acids or are nucleic acids. The sequences for the human analogs of these genes, as well as other analogs, and alleles of these genes, and splice variants and other types of variants, are available in a variety of protein and gene databases, including Genbank. Those sequences available at the time of filing this application at Genbank are herein incorporated by reference in their entireties as well as for individual subsequences contained therein. Genbank can be accessed at http://www.ncbi.nih.gov/entrez/query.fcgi. Those of skill in the art understand how to resolve sequence discrepancies and differences and to adjust the compositions and methods relating to a particular sequence to other related sequences. Primers and/or probes can be designed for any given sequence given the information disclosed herein and known in the art.

C. METHODS OF MAKING ECM MIMICKING NANOMATRIX

Also disclosed is a method of making an endothelium mimicking nanomatrix, comprising inducing self-assembly of one or more peptide amphiphiles disclosed herein into nanofibers. The self-assembly can be induced by, for example, drying a liquid composition comprising the one or more peptide amphiphiles on a solid surface. Other methods of inducing self-assembly of peptide amphiphiles are known in the art and can be used in the disclosed methods. For example, assembly can be induced by divalent ions (calcium chloride) or pH.

The disclosed method can further comprise reacting the one or more peptide amphiphiles with nitric oxide to form a diazeniumdiolate-modified peptide. For example, diazeniumdiolate-modified peptide can comprise the sequence $[K[N(O)NO^-]]_n$. In some aspects, n is from 1 to 20. In some aspects, n is 1, 2, 3, 4, 5, 6, 7, 8, 9, 10, 11, 12, 13, 14, 15, 16, 17, 18, 19, 20 or higher. Thus, the diazeniumdiolate-modified peptide can comprise the sequence $[K[N(O)NO^-]]_5$.

D. METHODS OF USING ECM MIMICKING NANOMATRIX

Also disclosed is a method comprising coating a medical device with an endothelium mimicking nanomatrix disclosed herein. The method can comprise inducing self-assembly of one or more peptide amphiphiles disclosed herein into nanofibers on the medical device. For example, the method can comprise drying a liquid composition comprising the one or more peptide amphiphiles on the medical device.

The medical device can be any device known or identified for use inside the body of a subject. Preferably, the medical device is one that is inserted into the cardiovascular system.

The medical device can comprise any material suitable for use as a surgical implant. For example, the medical device can comprise titanium alloy. The medical device can comprise cobalt-cromium. The medical device can comprise nickle-titanium. The medical device can comprise a biodegradable polymer.

In some aspects, the medical device is a vascular stent. For example, the stent can be a bare medal stent. In some aspects, the stent is a drug eluting stent. For example, the stent can be a sirolimus-eluting stent or a paclitaxel-eluting stent.

In some aspects, the medical device is a vascular graft. In some aspects, the medical device is a catheter. In some aspects, the medical device is a pacemaker. In some aspects, the medical device is a heart valve.

It is also contemplated that the disclosed endothelium mimicking nanomatrix compositions can further comprise one or more biologically active agent(s). For example, in one aspect, an endothelium mimicking nanomatrix can include an effective amount of one or more biologically active agent(s).

It is also contemplated that the disclosed endothelium mimicking nanomatrix compositions can further comprise one or more pharmaceutically active agent(s). For example, in one aspect, an endothelium mimicking nanomatrix can include an effective amount of one or more pharmaceutically active agent(s).

E. METHODS OF MAKING THE HYDROPHILIC PEPTIDES

The compositions disclosed herein and the compositions necessary to perform the disclosed methods can be made using any method known to those of skill in the art for that particular reagent or compound unless otherwise specifically noted.

1. Peptide Synthesis

One method of producing the disclosed proteins, such as SEQ ID NO:1 to SEQ ID NO:11, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W. H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269: 16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

2. Nucleic Acid Synthesis

Another method of producing the disclosed proteins, such as SEQ ID NO:1 to SEQ ID NO:11, is to produce a nucleic acid encoding the disclosed proteins operably linked to an expression control sequence. Such nucleic acids can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

F. METHODS OF MAKING PEPTIDE AMPHIPHILES

Also disclosed herein is a method of making a peptide amphiphile, comprising the steps: a) providing a hydrophilic peptide comprising a degradation sequence and one or more of an endothelial cell adhesive sequence and a nitric oxide producing donor sequence; and b) alkylating the N-terminus of the hydrophilic peptide with a hydrophobic moiety. In a further aspect, the alkylation can comprise amidation with a hydrophobic carboxylic acid. The hydrophobic carboxylic acid can be a fatty acid. The fatty acid can be palmitic acid.

It is contemplated that a disclosed amphiphile can be prepared by attachment of a hydrophobic moiety via conventional synthetic techniques. For example, a hydrophobic moiety can be attached at the N-terminus of the hydrophilic peptide. That is, hydrophobic electrophilic compounds (e.g., alkyl halide, carboxylic compound) can be reacted with the amine function present at the N-terminus to provide a covalent linkage (e.g., secondary or tertiary amine, amide).

In further examples, a hydrophobic moiety can be attached at the C-terminus of the hydrophilic peptide. That is, hydrophobic nucleophilic compounds (e.g., alcohol, amine, thiol) can be reacted with the carboxylic function present at the C-terminus to provide a covalent linkage (e.g., ester, amide, thioesters). It is further contemplated that the carboxylic function present at the C-terminus can be derivatized or reduced prior to reaction. For example, the carboxylic function can be reduced to form an alcohol and subsequently reacted with one or more hydrophobic electrophilic compounds (e.g., alkyl halide, carboxylic compound) to provide a covalent linkage (e.g., ether, ester).

As readily understood by those of skill in the art, peptide sequences can comprise peptide residues having one or more pendant groups. The pendant groups, in various aspects, can comprise one or more nucleophilic moieties (e.g., amine, hydroxyl, thiol) or one or more electrophilic moieties (e.g., carboxylic function). Such moieties can be reacted in a manner analogous to that disclosed above with respect to N-terminus and C-terminus of a disclosed hydrophilic peptide.

G. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 i. Materials and Methods a. Synthesis of Peptide Amphiphile

Two thirteen-amino acid peptides consisting of MMP-2 sensitive sequences (GTAGLIGQ; SEQ ID NO:1) with cell-adhesive sequence YIGSR (SEQ ID NO:2) ("PA-YIGSR") or NO donor sequence KKKKK (SEQ ID NO:3) ("PA-KKKKK") were synthesized using standard Fmoc-chemistry on an Advanced Chemtech Apex 396 peptide synthesizer. Alkylation was obtained by reacting N-termini of the peptides with 2 equivalents of palmitic acid, 2 equivalents of o-benzotriazole-N,N,N',N'-tetramethyluroniumhexafluorophosphate (HBTU), and 4 equivalents of diisopropylethylamine (DiEA) in dimethylformamide (DMF) for 12 h at room temperature. After repeating the alkylation reaction, cleavage and deprotection of PAs were performed using a mixture of trifluoroacetic acid (TFA), deionized (DI) water, triisopropylsilane, and anisole in the ratio of 90:1:1:1 for 3 hours at room temperature. The solution was concentrated using a rotary evaporator. PAs were precipitated in cold ether, collected, and dried under vacuum. The crude PA was dissolved in DI water at a concentration of 2 wt %. The PA was analyzed by matrix-assisted laser desorption ionization time-of-flight (MALDI-TOF) mass spectrometry.

b. Transmission Electron Microscope (TEM) Imaging

For TEM samples, 5 µl of each 0.1 wt % PA aqueous solution were cast on a carbon coated formvar copper grid (400 mesh). This grid was dried overnight. Before imaging, the dried samples were negatively stained with 10 µl of 20% phosphotungstenic acid (PTA) for 30 s. The samples were imaged (42000×, 52000×) on a FEI Tecnai T12 TEM microscope at 60 kV accelerating voltage.

c. Self-Assembly of Peptide Amphiphiles into Nanofibers 0.1 wt % stock solutions for PA-YIGSR and PA-KKKKK were prepared in DI water (pH 7.4) and mixed in a molar ratio of 9:1 ("PA-YK"). 50 µl of PA-YK solution per well were placed in 12-well silicone flexiPERM cell-culture chambers attached to glass coverslips. The chambers were placed in a chemical fume hood for 24 hours to induce self-assembly by solvent evaporation. The chambers were further dried for another 48 hours in a 37° C. incubator.

d. Cell Maintenance

Human umbilical vein endothelial cells (HUVECs) were grown in endothelium growth medium (EGM) complete medium (0.1% Gentamycin/Amphotericin B). This cell culture medium was used in all HUVEC experiments. Cells were passaged by trypsinizing (0.05% trypsin/EDTA) and subcultured at a density of 2500-5000 cells/cm$^2$. Human aortic smooth muscle cells (AoSMCs) were grown in smooth muscle cell basal medium (SmBM) SINGLEQUOT® Kit complete culture medium (0.1% Gentamycin/Amphotericin B). This cell culture medium was used in all AoSMC experiments. Cells were passaged by trypsinizing (0.05% trypsin/EDTA) and subculturing at a density of 3500 cells/cm$^2$. All cell cultures were maintained under standard culture conditions (37° C., 95% relative humidity, and 5% CO$_2$). All cells and media were purchased from Lonza Inc. (Walkersville, Md.).

e. Initial Attachment and Spreading of HUVECs and AoSMCs on PA-YK Nanomatrix

PA-YK nanomatrix coated culture chambers were prepared as disclosed herein. For initial cell attachment, HUVECs and AoSMCs were seeded on PA-YK nanomatrix coated culture chamber at densities of 30,000 cells/cm$^2$ and 15,000 cells/cm$^2$, respectively. After 2 hours of incubation cells were stained with Calcein AM green fluorescent dye and Ethidium homodimer-1 red fluorescent dye using LIVE/DEAD Viability/Cytotoxicity Kit (Molecular Probes, Eugene, Oreg.). The number of attached cells per field of view (20×) was determined using fluorescent microscopy (Nikon Eclipse E2000), and by averaging five random fields were averaged per sample. The individual cell spreading was analyzed by image processing software (NIS-elements AR 2.30).

f. Platelet Adhesion on PA-YK and PA-YK-NO Nanomatrix

PA-YK and PA-YK-NO solution was prepared as described herein and cast into films by dropping 150 µl of the solution on 13 mm circular glass cover slips. A solution of 2.5 mg/ml collagen I was prepared in 3% glacial acetic acid and cast into films in the same manner to serve as the control surface. Whole blood from a healthy volunteer was collected in BD VACUTAINER® Heparin Tubes (BD, NJ) and mixed with 10 uM mepacrine to fluorescently label the platelets. Before the experiment, PA-YK, PA-YK-NO, and collagen films were rinsed with PBS. Thereafter, collagen I, PA-YK, PA-YK-NO films were separately incubated with mepacrine-labeled blood at 37° C. for 15 minutes and then rinsed with PBS. The number of adherent platelets per field of view (40×) was determined using a fluorescent microscope (Nikon Eclipse E2000) by averaging five random fields per sample.

g. Preparation of scrubbed NO

Figure 4:
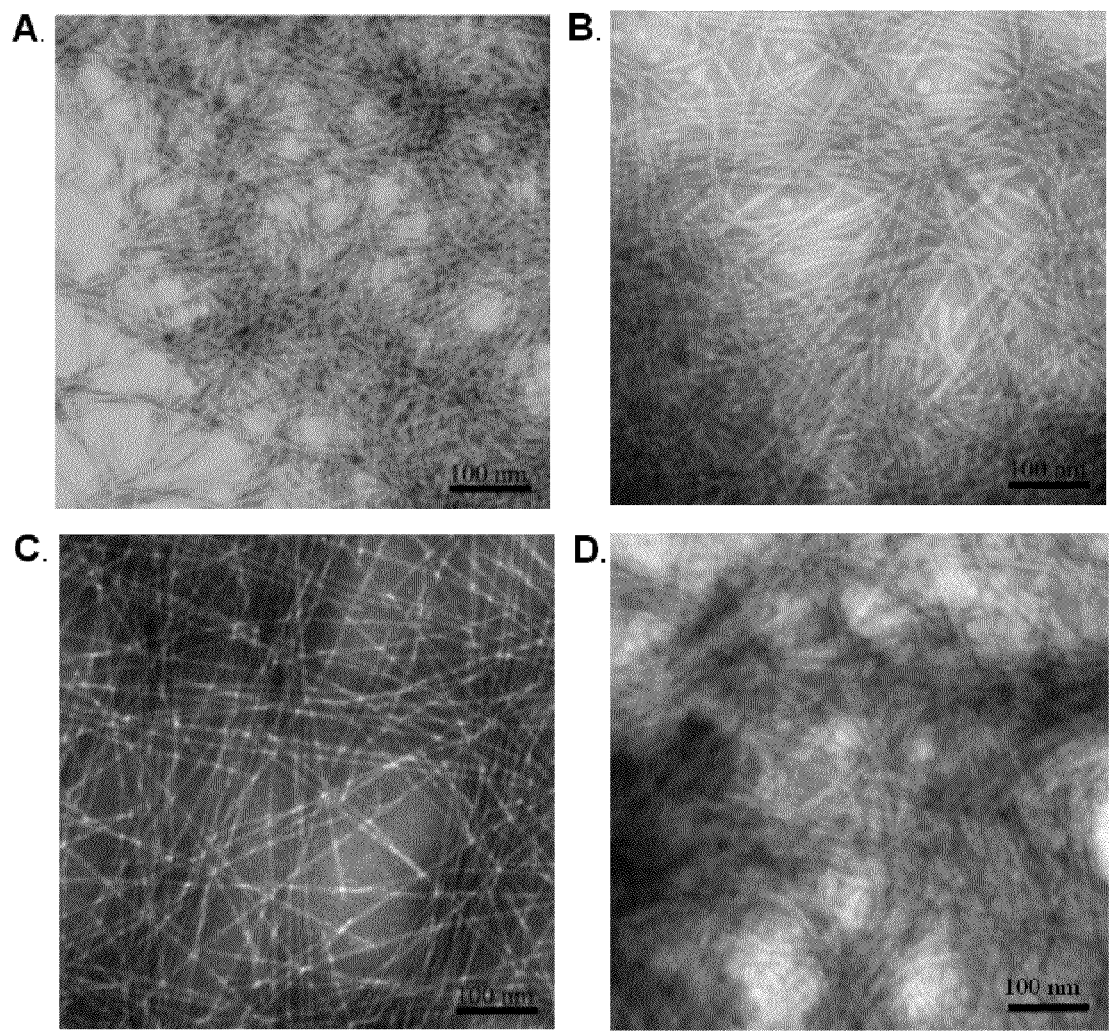
FIG. 4 shows TEM images of evaporation induced self-assembled nanofibers. Shown are PAs YIGSR (SEQ ID NO: 2) "PA-YIGSR" (A), KKKKK (SEQ ID NO: 3) "PA-KKKKK" (B), PA-YK (C), and PA-YK-NO (D).

First, the NO solution can be scrubbed. Scrubbing is a process by which a gas is passed through a large surface area of a liquid to remove the unwanted impurities from the gas stream. In this case, the commercially available nitric oxide is passed through an alkaline solution which dissolves the unwanted higher nitrogen oxide species. The apparatus shown in FIG. 4 was first degassed with Argon. NO was scrubbed through a 5 M NaOH solution and collected in a reaction vessel containing PA-YK solution.

h. Synthesis of NO Releasing Nanomatrix (PA-YK-NO)

"PA-YK-NO" was synthesized by reacting PA-YK with scrubbed NO under argon gas. 0.1 wt % PA-YK aqueous solution was reacted with scrubbed NO solution at room temperature under argon gas in 100 mL round bottom flask overnight. The resulting PA-YK solution was cast into films by dropping 130 µl on 13 mm glass cover slips. The films were dried in a chemical fume hood for first 24 hours and at 37° C. for next 48 hours. In order to determine NO release profile, each PA-YK-NO film was incubated in 500 µl of HBS in a 24 well tissue culture plate (Corning Inc., Corning, N.Y.). The HBS was collected, frozen (−20° C.) and replaced by fresh HBS at different time points over 1 months. NO release from the PA-YK-NO nanomatrix was then confirmed and quantified using the Greiss assay, containing sulfanilamide and N-1 napthylethylenediamine dihydrochloride (Promega, Wis.) to measure the nitrite content, which is the principle degradation product of NO.56. At the end of day 5 each collected sample was mixed with 100 µl of the Griess reagent. After incubation for 15 minutes at room temperature, the samples were read at 540 nm using an absorbance microplate reader (EL×800, BIO-TEK Instrument, VT).

i. Evaluation of Proliferation of HUVECs and AoSMCs on PA-YK-NO Nanomatrix

PA-YK-NO and PA-YK films were prepared as describe herein, and sterilized under UV for 4 hours. Proliferation of HUVECs and AoSMCs was evaluated by proliferating cell nuclear antigen (PCNA) staining. PCNA is a 36 kDa non-histone protein found in the nucleus that plays a role in the initiation of cell proliferation. Its prominent presence in nucleoli during the late S phase of the cell cycle makes it an ideal marker for cell proliferation. HUVECs and AoSMCs were seeded at densities of 30,000 cells/cm$^2$ and 15,000 cells/cm$^2$, respectively. Cells were incubated under standard culture conditions (37° C., 95% relative humidity, and 5% $CO_2$). After 48 hrs of incubation, cells were fixed in a 10% neutral buffered formalin solution (Sigma Chemical Co., St. Louis, Mo.) and rinsed with PBS. The cells were then permeabilized by incubating in histological grade methanol (Sigma Chemical Co., St. Louis, Mo.), followed by rinsing with PBS. A 3% hydrogen peroxide solution was used to block endogenous peroxidases. After rinsing with PBS, the cells were then incubated with tris-buffered saline, followed by incubation with mouse IgG anti-PCNA primary antibody (Dako Corp., Carpinteria, Calif.) diluted 1:100 in phosphate-buffered saline (PBS) with 3% FBS. After aspirating the primary antibody and rinsing with PBS, the cells were incubated with anti-mouse IgG HRP (Dako Corp., Carpinteria, Calif.) diluted 1:100 in PBS with 3% FBS, followed by incubation with aminoethylcarbazole chromogen (Dako Corp., Carpinteria, Calif.). The chromogen generates a red precipitate representing the proliferating cells. The cells were then rinsed with PBS and counterstained with Mayer's hematoxylin. Excess hemotoxylin was washed away by rinsing the samples with 37 mM ammonium hydroxide 2-3 times. The percentage of proliferating cells per field of view (20×) was determined by counting the red proliferating cells and hemotoxylin stained blue non-proliferating cells using phase contrast microscopy (Nikon Eclipse E2000) after averaging five fields per sample.

j. Statistical Analysis

All data were compared with one-way ANOVA tests using SPSS software. A p value less than 0.05 was considered to be statistically significant.

ii. Results a. Self-Assembly of Peptide Amphiphiles into Nanofibers

PA-YIGSR and PA-KKKKK were successfully synthesized, and their molecular weights were confirmed by MALDI-Tof mass spectrometry. A hybrid peptide amphiphile of PA-YIGSR and PA-KKKK ("PA-YK") was synthesized by mixing 0.1 wt % solutions of PA-YIGSR and PA-KKKKK in a molar ratio of 9:1. The self-assembly of the PAs into the nanofibers was induced by evaporating the solvent as described earlier. NO releasing PA-YK-NO was synthesized by further reacting PA-YK with NO under argon. The TEM images (FIG. 4) demonstrate successful self-assembly of PAs into nanofibers by solvent evaporation. The nanofibers obtained were similar in dimension to those previously reported in self-assembly studies using divalent ion or pH change.

b. Evaluation of Initial Cell Attachment and Spreading

Figure 5:
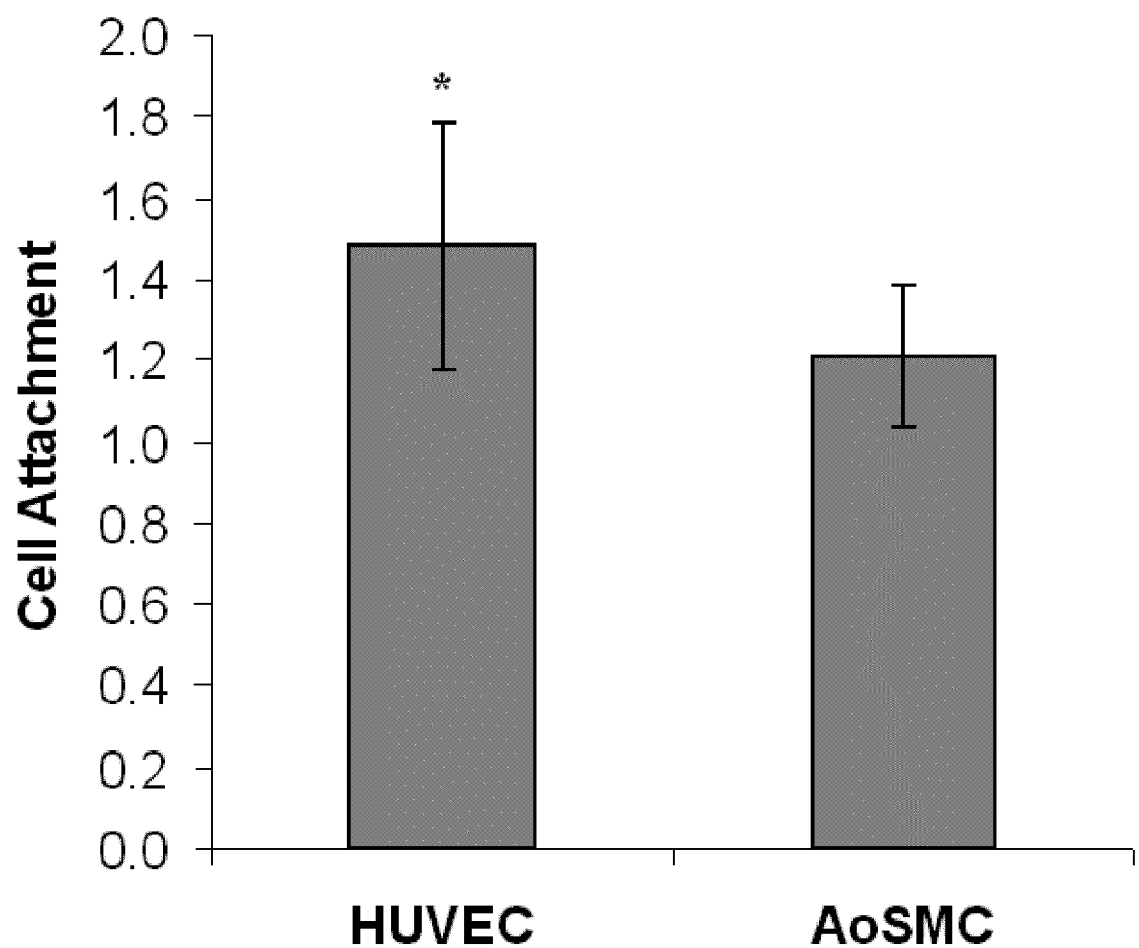
FIG. 5 shows initial attachment of HUVECs and AoSMCs on PA-YK (9:1 molar ratio of PAs YIGSR (SEQ ID NO: 2) "PA-YIGSR" and KKKKK (SEQ ID NO: 3) "PA-KKKKK") nanomatrix. Cell attachment is normalized to that of attachment on the glass. *HUVECs show significantly higher attachment than AoSMCs after 2 hrs (p<0.05). Error bar represents means±standard deviation for n=12.
Figure 6:
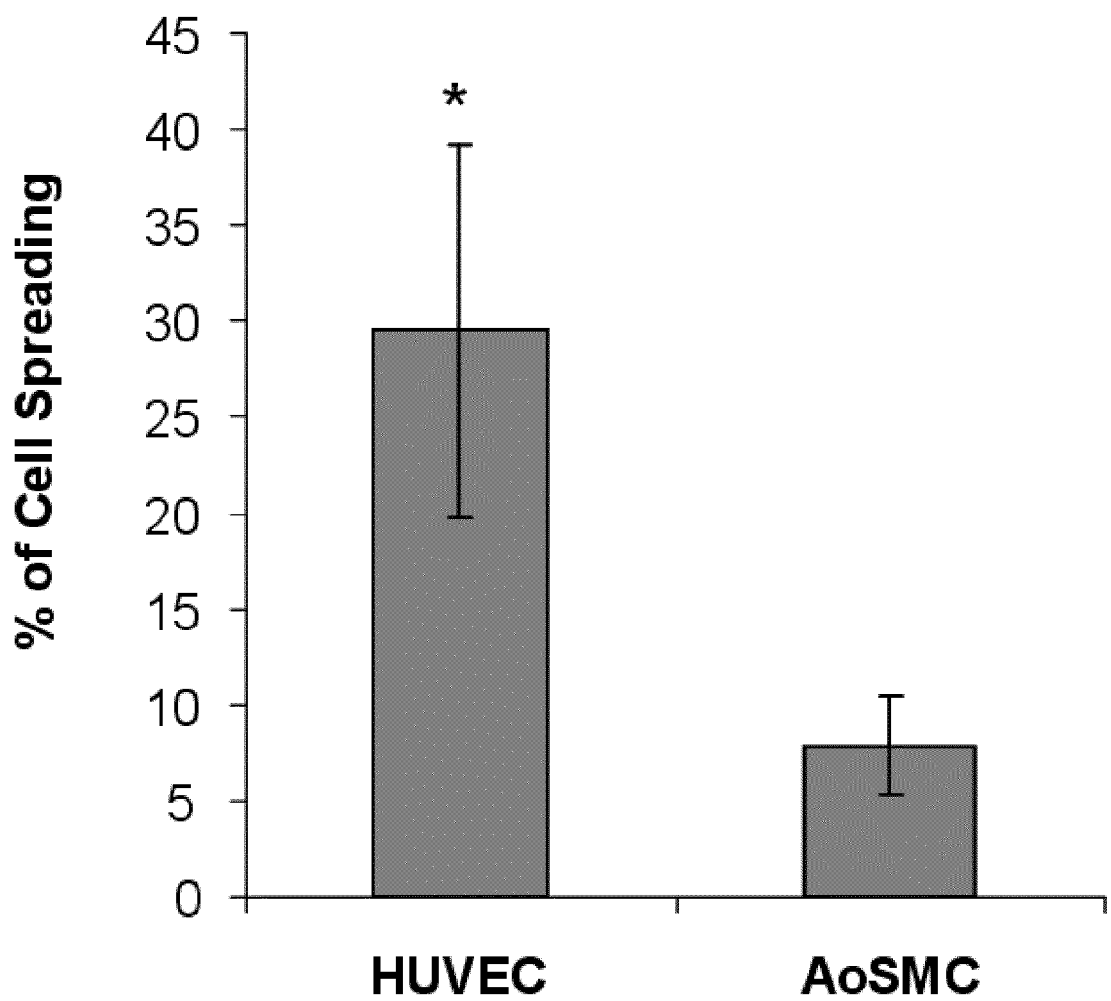
FIG. 6 shows initial spreading of HUVECs and AoSMCs on PA-YK coatings. *HUVECs show significantly greater spreading than AoSMCs after 2 hrs (p<0.01). Error bar represents means±standard deviation for n=12.
Figure 7:
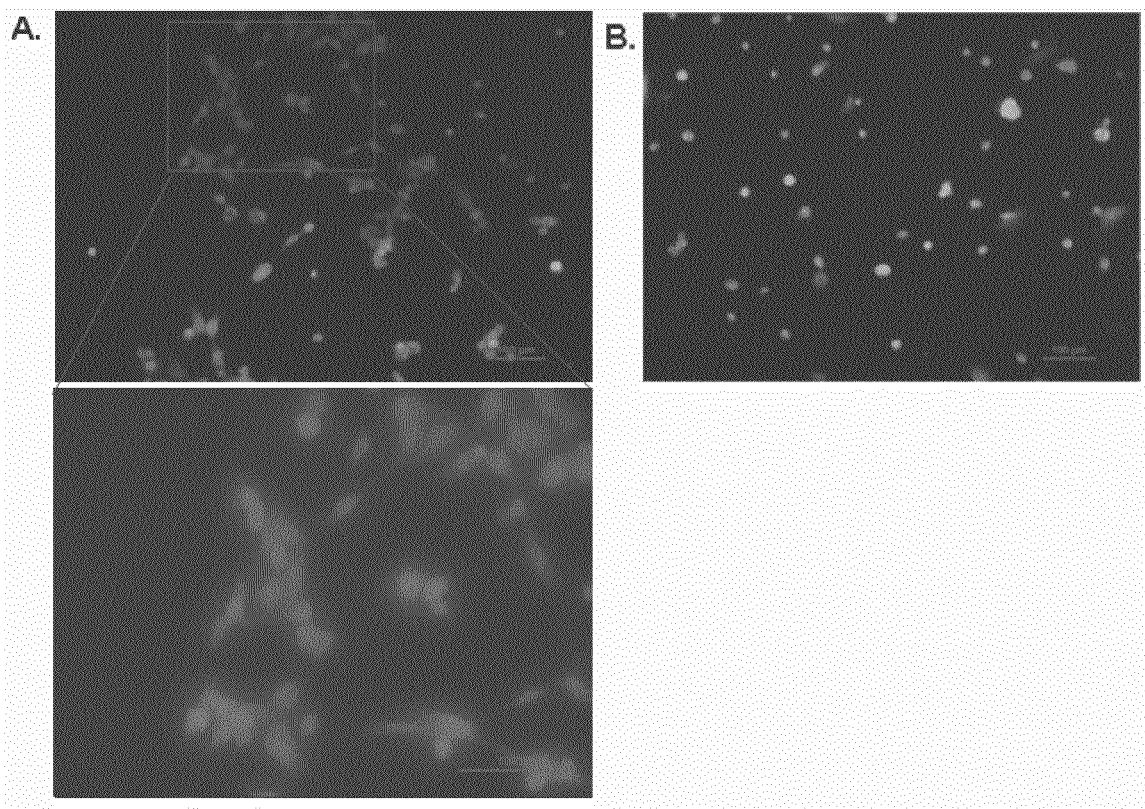
FIG. 7 shows fluorescent images of HUVECs and AoSMCs on PA-YK after 2 hours using Calcein AM.

Both HUVECs and AoSMCs were separately seeded on the PA-YK nanomatrix and cell attachment was evaluated to determine whether endothelial cells recognize the adhesive ligand YIGSR in the nanomatrix. Initial attachment of HUVECs was found to be slightly higher than compared to AoSMCs (FIG. 5). This was confirmed by evaluating the spreading of HUVECs and AoSMCs on the PA-YK nanomatrix after 2 hours (FIGS. 6 and 7). After 2 hours, HUVECs were found to spread three fold more than AoSMCs. The results indicate that HUVECs can recognize the YIGSR incorporated into the PA-YK, signifying that PA-YK nanomatrix promotes HUVEC attachment and spreading.

c. Evaluation of Attachment of Platelets and on PA-YK Nanomatrix

Figure 8:
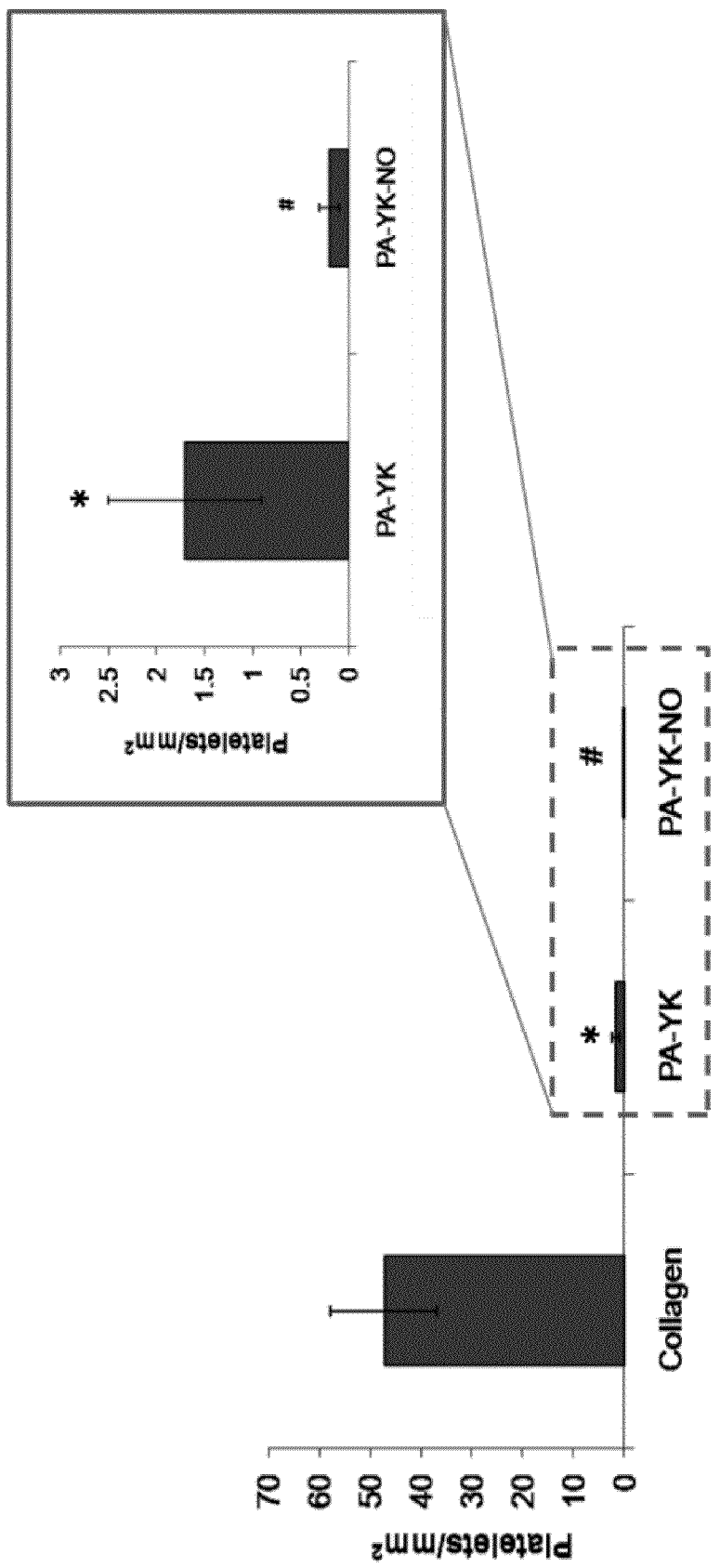
FIG. 8 shows platelet attachment on Collagen, PA-YK, and PA-YK-NO nanomatrices after incubation with human blood for 15 minutes. Platelet adhesion is significantly less on PA-YK-NO films compared to PA-YK or collagen I-coated films. Data represent the mean of three samples. Error bar represents mean±standard deviation. (*: p<0.05 compared to collagen I; #: p<0.05 compared to PA-YK).

Platelet attachment on PA-YK-NO and PA-YK nanomatrix was evaluated using mepacrine-labeled whole blood. Platelet adhesion was approximately 50-fold lower on PA-YK nanomatrices compared to the positive control, Collagen I. Furthermore, exposure of blood to NO-releasing PA-YK-NO nanomatrices resulted into virtually no platelet attachment. (FIG. 8)

d. NO Release from PA-YK-NO Nanomatrix

Figure 10:
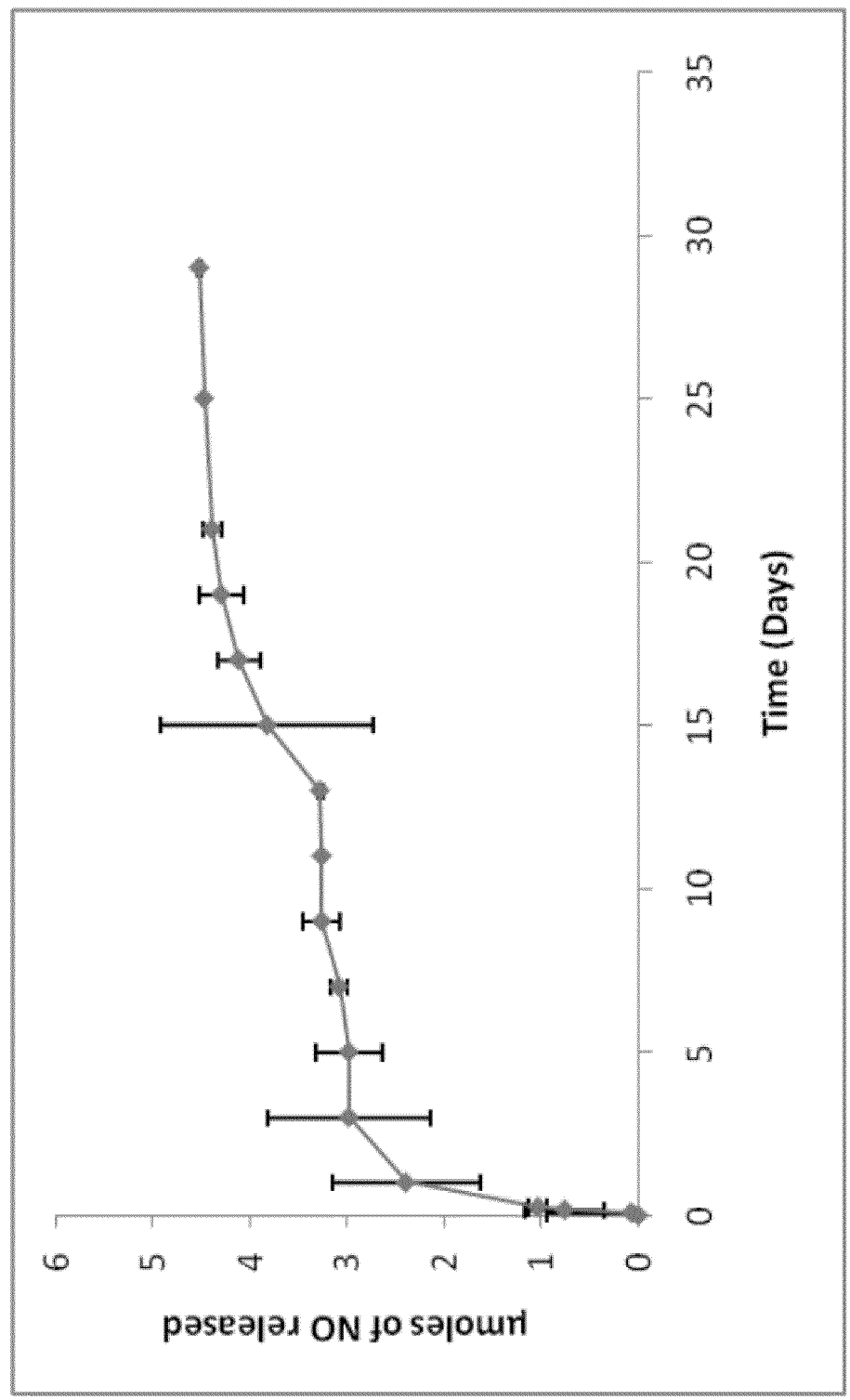
FIG. 10 shows NO release from PA-YK-NO films in HBS at pH 7.4, 37° C. 53% of total NO released displaying multiphasic profile over one month. Data represent the mean of four samples. Error bar represents mean±standard deviation.

The NO release profile from the PA-YK-NO nanomatrix over a period of one month is shown in FIG. 10. Most of the NO was released in the first 24 hours, followed by a slow sustained release over a period of two weeks, followed by another burst release resulting in recovery of about 53% NO. The value of 100% NO (8.6 μmoles) is calculated by assuming that every lysine residue in PA-YK reacts with two molecules of NO.

e. Evaluation of Proliferation of HUVECs and AoSMCs on PA-YK-NO Nanomatrix

Figure 9:
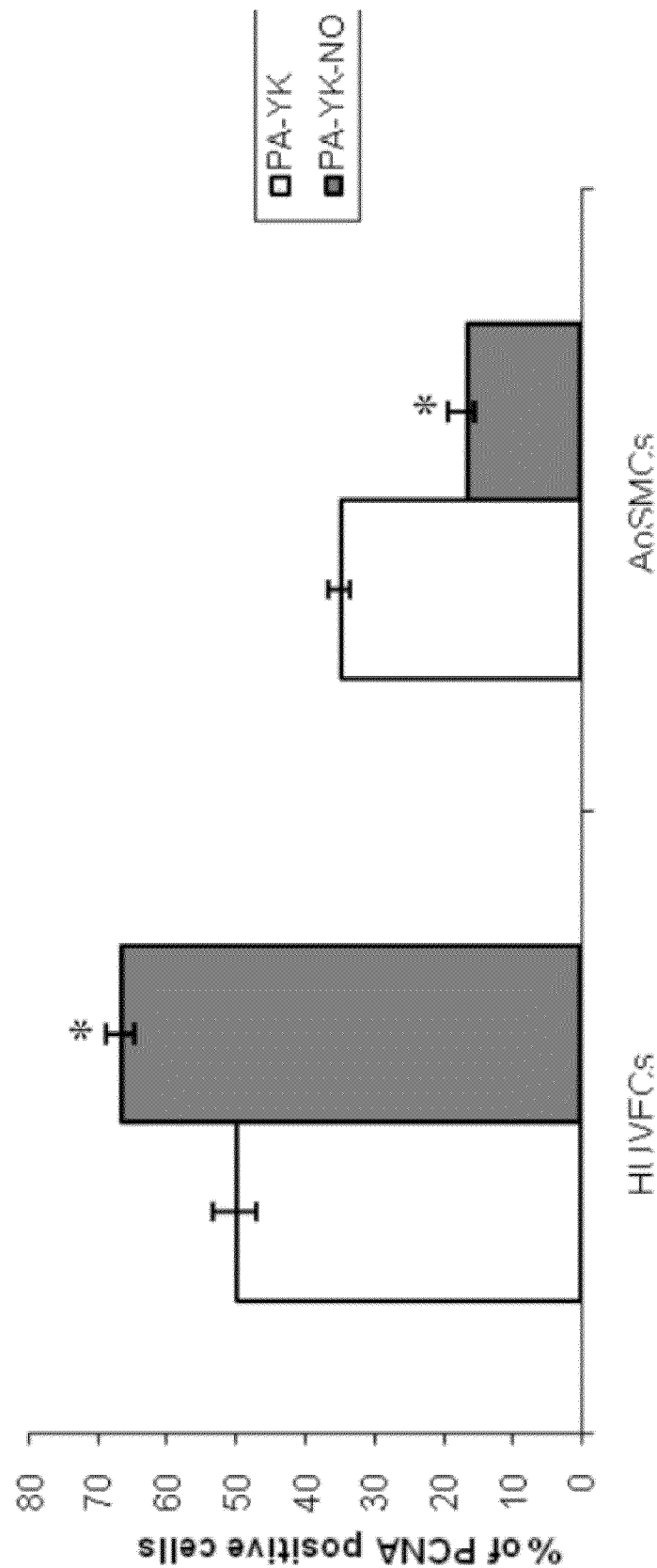
FIG. 9 shows proliferation of HUVECs and AoSMCs seeded on PA-YK and PA-YK-NO nanomatrices after 48 hours, quantitatively assessed by PCNA staining. PA-YK-NO enhances HUVECs proliferation but reduces AoSMCs proliferation. Results are expressed as the percentage of PCNA positive cells. Data represent the mean of four samples. Error bar represents mean±standard deviation. (*, #: p<0.05).

To examine the effect of NO on HUVECs and AoSMCs, the cells were seeded on PA-YK-NO nanomatrix coated culture chambers. The proliferation of the cells was evaluated using PCNA staining after 48 hours of incubation. Parallel proliferation experiments were also conducted on PA-YK nanomatrix as a control. As shown in FIG. 9, the percentage of PCNA positive HUVECs ((66.8±1.94)%) on PA-YK-NO was found to be significantly greater as compared to PA-YK ((50.29±3.4)%). Conversely, the percentage of PCNA positive AoSMCs on PA-YK-NO ((16.4±2.8)%) was significantly lower than that on PA-YK ((34.8±1.9)%).

2. Example 2

In Vivo Evaluation of Native Endothelium Mimicking Self-Assembled Nanomatrix

Self-assembled nanomatrix coated stents were implanted in rabbit iliac arteries and evaluated by histomorphometry for evidence of stenosis and thrombosis.

i. Materials and Methods a. Stent Coating and Characterization

Figure 11:
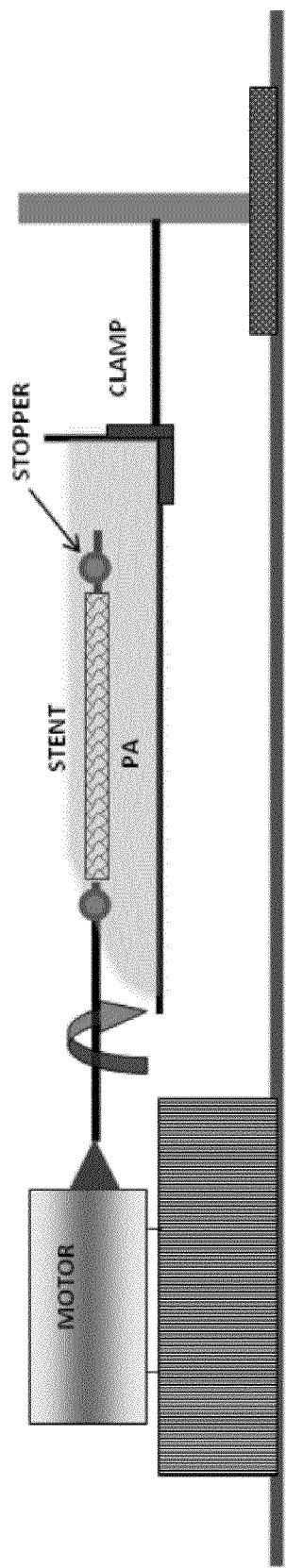
FIG. 11 shows Schematic representation of stent coating technique with nanomatrix.
Figure 12:
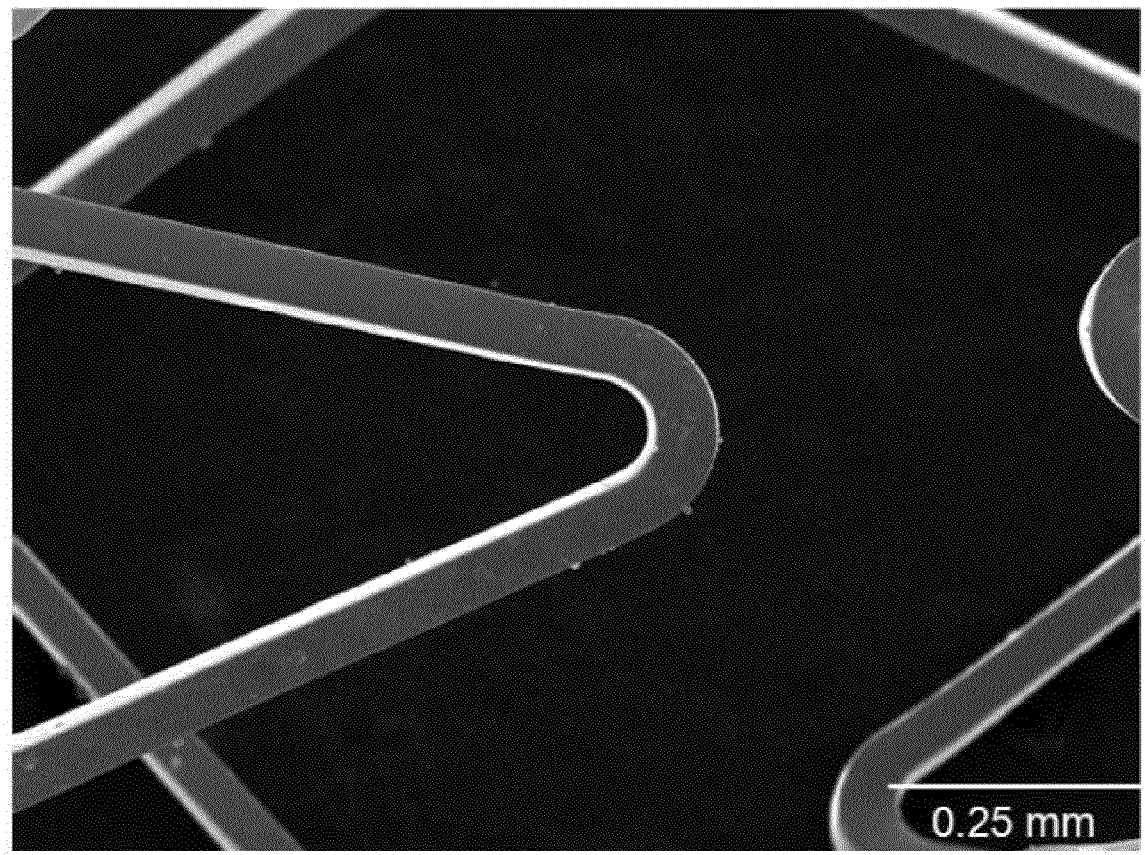
FIG. 12 shows SEM Image of 0.1 wt % PAYK coated stent after handling by the clinician. Notice the smooth uniform coating surface which stays undisturbed after handling (mounting on angioplasty balloon and expansion).

For uniform coating with the PA solution, a commercially available stainless steel stent was mounted on a mandrel (stainless steel wire—0.018 inches diameter) attached to a motor rotating at a speed of 15 rpm. The rotating stent was immersed in a PA solution contained in an open-top reservoir as shown in FIG. 11. The open-top reservoir facilitates evaporation induced self-assembly of PA into nanomatrix on the surface of the stent. Rotation of the stent ensures uniform coating of PA nanofibers throughout the outer and inner surfaces of the stent. The stoppers at both ends of the stents prevent the stent from sliding on the mandrel. The stent was rotated for 12 hours in the PA solution and then allowed to dry for another 24 hours. FIG. 12 shows the SEM image of 0.1 wt % PAYK coated stent after handling by the clinician. It is noted that the smooth uniform coating surface stays undisturbed after handling (mounting on angioplasty balloon and expansion). This result indicates that the PA nanomatrix can be uniformly coated onto stents and remain stable during the handling process.

b. Study Groups for In Vivo Assessment

Male white New Zealand Rabbits were used for this study. One rabbit was used per group with two stents implanted per rabbit. There were 2 different nanomatrix coatings and 1 uncoated bare metal stainless steel stent evaluated. Each stent type was evaluated at 2 weeks and 4 weeks as follows: Control (bare metal stent) 2 weeks, 4 weeks; Low dose (0.1 wt % PAYKNO coated) 2 weeks, 4 weeks; and High dose (1 wt % PAYKNO coated) 2 weeks, 4 weeks. For the two week time points, all the stents were implanted without prior balloon injury. All rabbits were housed for at least two days before the surgery. Surgery protocol was approved by Institutional Animal Care and Use Committee (IACUC) at University of Alabama at Birmingham, and is described below.

c. Stent Implantation

The day of the procedure, the rabbits were anesthetized with ketamine/xylazine 35/5 mg/kg. An endotracheal tube was inserted and connected to a respirator operated with a tidal volume of 400 ml at a rate of 16 breaths per minute. Anesthesia was sustained with isoflurane 2%. Heart rate and blood oxygen saturation was monitored using a pulse-oxymeter placed on the animal's tongue. Blood pressure was continuously monitored using a cuff on a hind limb. The rabbit was secured to the table in the dorsal recumbent position. 81 mg/day of aspirin by mouth was given daily, starting the day before the procedure, until the time of euthanasia.

The right carotid artery was surgically exposed and vascular access was obtained. A 6 French Sheath was inserted into the carotid artery and heparin (150 units/kg) was administered intravenously. Under fluoroscopic guidance, a 6 French JR4 coronary guide catheter was advanced over a 0.014" coronary guide wire to the descending aorta. Angiography was performed using approximately 8 ccs of Meglumine diaztroate contrast injected via the catheter. The baseline arteriogram was recorded digitally. Following angiography, a stent mounted on a delivery balloon was advanced over the guide wire into one iliac artery. The stent was deployed to be slightly oversized, with a stent to artery ratio of 1.1 to 1. A second stent was deployed in a similar manner in the other iliac artery. After stent implantation, the catheter, guidewire, and arterial sheath were removed. The carotid artery was ligated. The wound was sutured closed. The animal was then allowed to recover under observation. Buprenex (0.05 mg/kg) was administered intramuscularly every 12 hours, starting at the completion of the procedure.

Animals were monitored daily for any significant appetite loss/weight loss (more than 20% body weight loss), and lack of blood circulation in the lower limbs.

d. Stent Harvest 2 weeks and 4 weeks after stent implantation euthanasia was performed and the stented iliac arteries were pressure perfusion fixed with formalin. The stents were removed and placed in 10% buffered formalin for histological studies.

e. Tissue Processing

All fixed stents were dehydrated and embedded in methylmethacrylate resin. After complete polymerization, the areas of interest were brought closer to the surface by preliminary grinding. The opposite side of the block was mounted on a slide using Technovit 4000 (Exakt Technologies, Inc., Oklahoma City, Okla.). Sections (about 100 microns thick) are cut from each specimen using the Exakt Diamond Saw (Exakt Technologies, Inc., Oklahoma City, Okla.), which is somewhat like a large band saw that utilizes a diamond-coated cutting band with a water-cooling and flushing system. The sections were grounded to about 20-30 μm with the Exakt Grinding System (Exakt Technologies, Inc., Oklahoma City, Okla.), which produces precision parallel surfaces, and was smoothed using increasing grits of sandpaper. After the surface of the specimen to be studied was reached, it was polished with 4000 grit sandpaper to create as smooth a surface a possible. Sections were made at 25%, 50% and 75% regions of the stent. All sections were stained with Methylene Blue/Basic Fuchsin stain.

Histological analysis included injury, thrombus formation, inflammation, and the presence of neointima. The stented segments were analyzed and graded for arterial injury, using the Schwartz injury score. Inflammation and thrombus was also assessed around each strut, with a grading scale. Neointimal thickness at each strut was measured in microns. Computer-guided morphometric measurements were performed using digital images and Bioquant image analysis software (Bioquant Image Analysis Corp, Nashville, Tenn.). Computerized planimetry was performed.

ii. Results

Figure 13A:
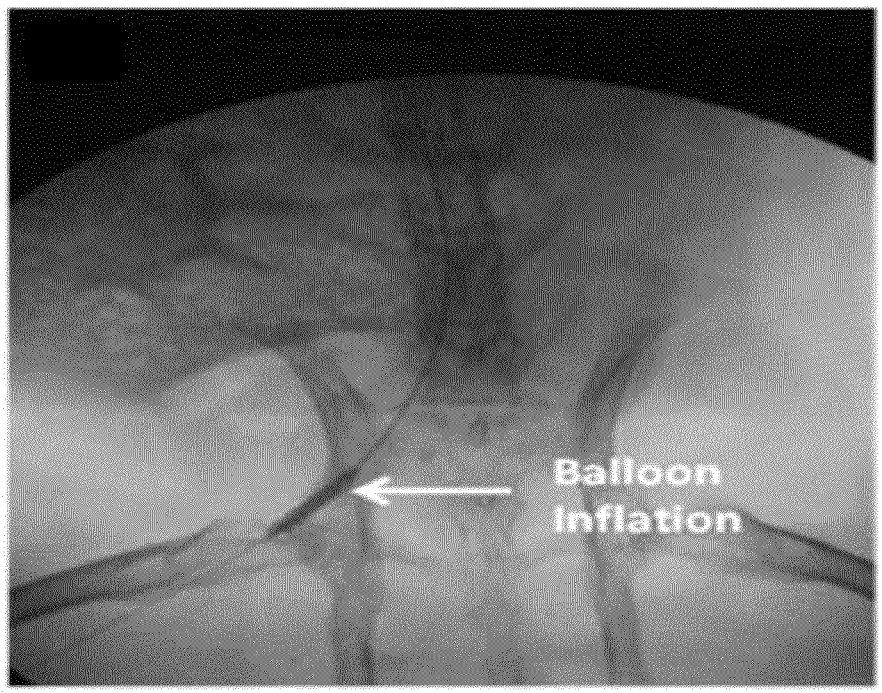
FIG. 13A shows balloon inflation to deploy stent in rabbit iliac artery.
Figure 13B:
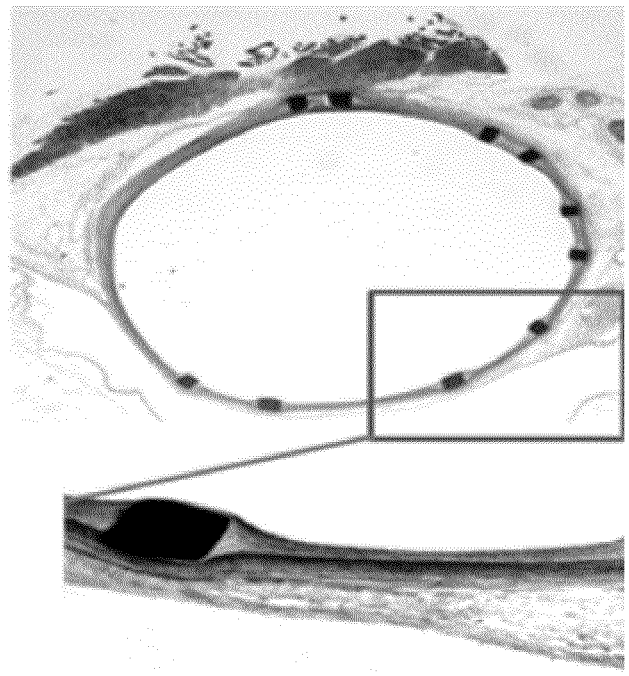
FIG. 13B shows histology section of 1 wt % nanomatrix coated stent after 4 weeks of implant. Little neointimal hyperplasia and no thrombus found on the surface of the nanomatrix coated stents.

FIG. 13A shows that balloon inflation successfully deployed stents in rabbit iliac artery. As shown in FIG. 13B, the stents were overall deployed fully and there was minimal underlying tissue injury. Blood vessels were intact and patent. No flaking or peel off of the nanomatrix coating was noted. Minimal inflammation was found around the stent struts. Notably, there was very little neointimal hyperplasia and no thrombus found on the surface of the nanomatrix coated stents.

Injury scores were assigned at each stent strut from 0 to three as follows: 0=no injury; 1=break in the internal elastic membrane; 2=perforation of the media; and 3=perforation of the external elastic membrane to the adventitia.

The average injury score for each segment was calculated by dividing the sum of injury scores by the total number of struts at the examined section. With the exception of control stents in 4 weeks group (average injury score ~0.02), no evidence of injury was seen in any stent.

Figure 14:
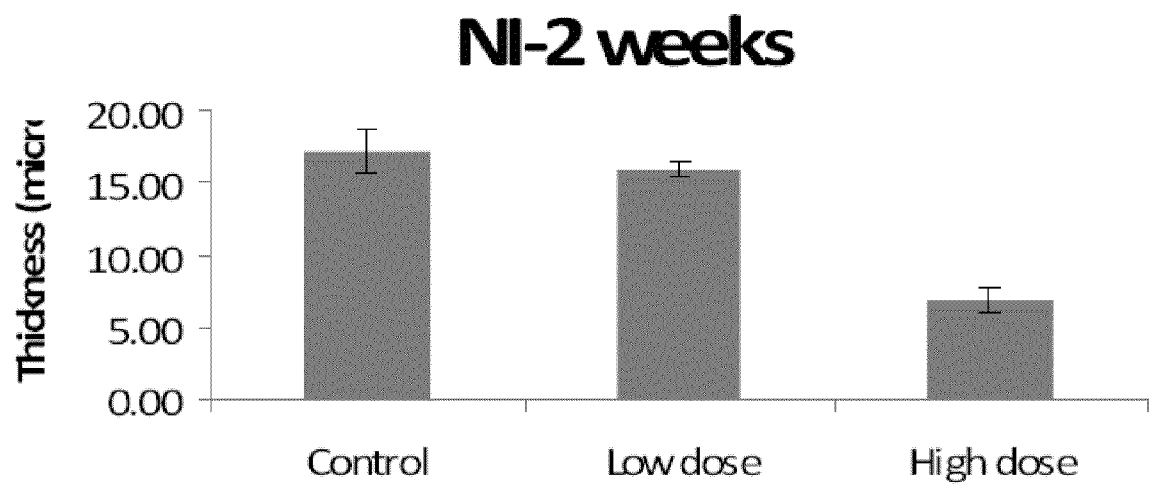
FIG. 14 shows neointimal thickness at 2 weeks. Apparent trend towards less NI thickness in the high dose stents compared to the control was observed. N=2 stents per group.
Figure 15:
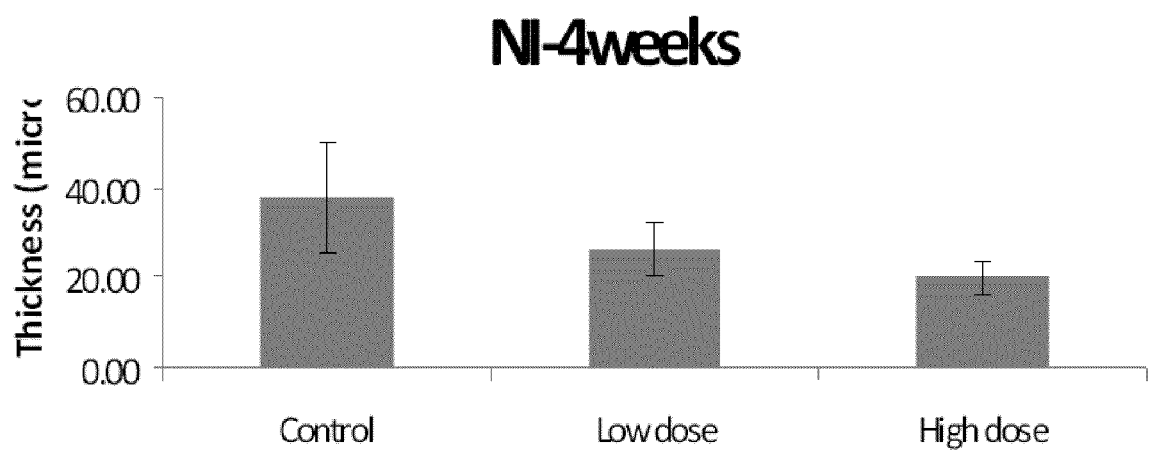
FIG. 15 shows neointimal thickness at 4 weeks. NI was greater than at 2 weeks, but the trend towards less NI in both the low dose and high dose groups appeared to persist, compared with controls. N=2 stents per group.

Neointimal Thickness (NI) was measured in microns. At 2 weeks as shown in FIG. 14, there appeared to be a trend towards less NI thickness in the high dose stents compared to the control. At 4 weeks NI as shown in FIG. 15, was greater than at 2 weeks, but the trend towards less NI in both the low dose and high dose groups appeared to persist, compared with controls.

Inflammation around each strut was assessed using the following grading scale: 0=no inflammatory cells surrounding the strut; 1=light, noncircumferential lymphohistocytic infiltrate surrounding the strut; 2=localized, moderate to dense cellular aggregate surrounding the strut noncircumferentially; and 3=circumferential dense lymphohistiocytic cell infiltration of the strut.

Figure 16:
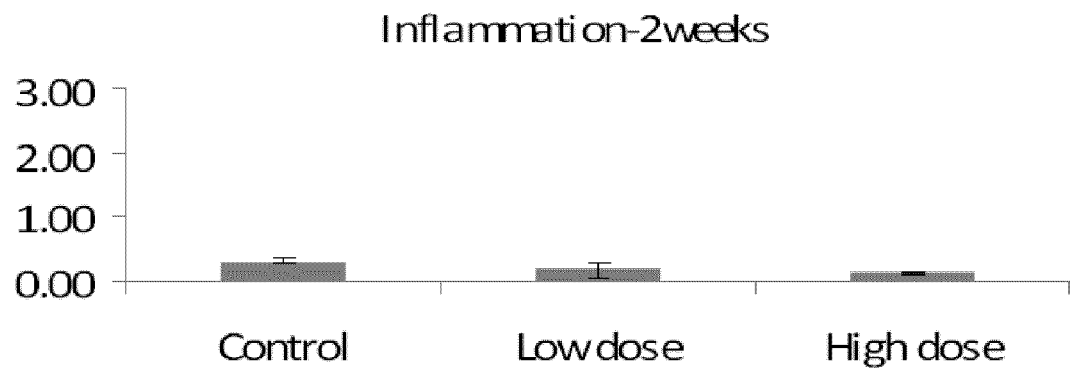
FIG. 16 shows inflammation scores at 2 weeks. Average inflammation scores for all study groups were less than 0.5. N=2 stents per group.
Figure 17:
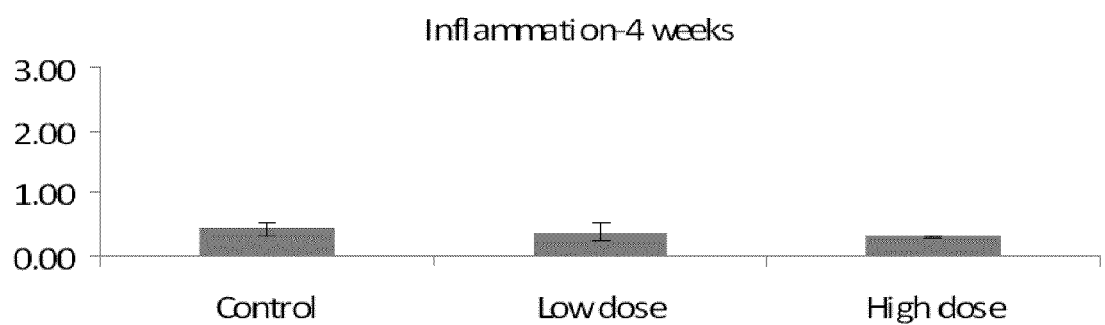
FIG. 17 shows inflammation scores at 4 weeks. Average inflammation scores for all study groups were less than 0.5. N=2 stents per group.

Average inflammation scores for all study groups were less than 0.5 with no significant differences in any of the 2 weeks for 4 weeks stent groups. Also, inflammation scores were found to be similar for both 2 weeks and 4 weeks groups as shown in FIGS. 16 and 17.

Figure 18:
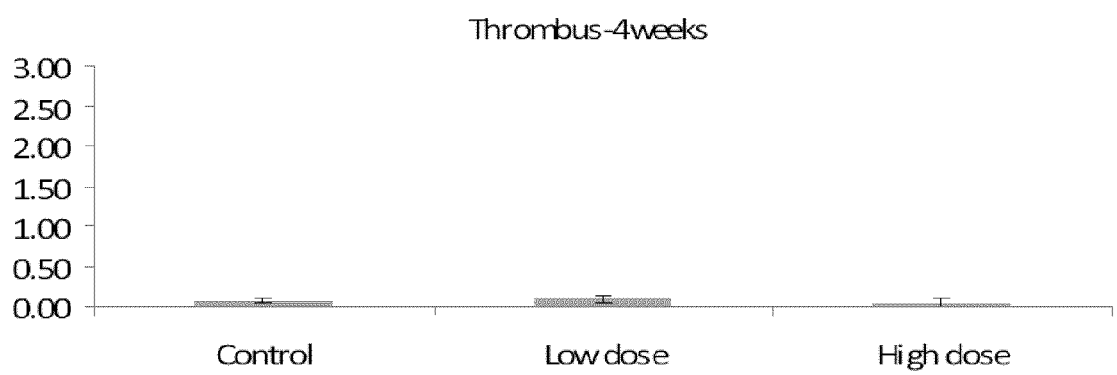
FIG. 18 shows thrombus scores at 4 weeks. The average thrombus score was less than 0.1 for all stent groups with no significant difference between the groups. N=2 stents per group.

Thrombus scores around each strut were scaled from zero to three. At 2 weeks there was minimal or no thrombus found in all stents. At 4 weeks the average thrombus score was less than 0.1 for all stent groups with no significant difference between the groups. One of the two high dose stent displayed no thrombus at 4 weeks as shown in FIG. 18.

iii. Conclusions

Overall, all animals survived and there was a minimal tissue injury associated with the stent deployment in all groups. Stent coating seems to be stable as no flaking or peel off of the nanomatrix coating was noted. There was minimal inflammation and almost no thrombus observed at both the 2 week and 4 week time points. A comparison of neointimal thickness across the groups showed no appreciable differences among any group, although there was a suggestion of a decreasing trend in the high dose and low dose stent groups compared to the uncoated control stent groups. Endothelial cells were observed on the histology sections including the high dose stents. The absence of fibrin deposition and no consequent thrombus around the struts can be due to presence of endothelial cell lining on the surfaces.

H. REFERENCES

Ross J M. Cell-extracellular matrix interactions. In: Patrick C W, Mikos A G, McIntire L V, eds. Frontiers in Tissue Engineering: Elsevier Science Inc.; 1998.

Alsberg E, Kong H J, Hirano Y, Smith M K, Albeiruti A, Mooney D J. Regulating bone formation via controlled scaffold degradation. J Dental Res. 2003; 82 (11):903-908.

Bryant S J, Anseth K S. Hydrogel properties influence ECM production by chondrocytes photoencapsulated in poly (ethylene glycol) hydrogels. J Biomed Mater Res. 2002; 59:63-72.

Heart Disease and Stroke Statistics—2007 Update. Circulation. 2007; 115:e69-e171.

Silverthorn D U. Blood flow and the control of blood pressure. Human Physiology. 3 ed. San Francisco: Benjamin Cummings Inc.; 2004:490-522.

Windecker S, Meier B. Intervention in coronary artery disease. Heart. 2000; 83:481-490.

Sheiban I, Carrieri L, Catuzzo B, Destefanis P, Oliaro E, Moretti C, Trevi G P. Drug-eluting stent: the emerging technique for the prevention of restenosis. Minerva cardioangiologica. 2002; 50 (5):443-453.

Dobesh P P, Stacy Z A, Ansara A J, Enders J M. Drug-eluting stents: a mechanical and pharmacologic approach to coronary artery disease. Pharmacotherapy. 2004; 24 (11): 1554-1577.

Ozaki Y, Violaris A G, Serruys P W. New stent technologies. Prog Cardiovasc Dis. 1996; 39 (2): 129-140.

Violaris A G, Ozaki Y, Serruys P W. Endovascular stents: a 'break through technology', future challenges. Int J Card Imaging. 1997; 13 (1):3-13.

Bauters C, Isner J M. The biology of restenosis. Prog Cardiovasc Dis. 1997; 40 (2):107-116.

Ong A T, Serruys P W. Technology Insight: an overview of research in drug-eluting stents. Nat Clin Pract. 2005; 2 (12):647-658.

Acharya G, Park K. Mechanisms of controlled drug release from drug-eluting stents. Adv Drug Deliv Rev. 2006; 58:387-401.

de Man F H, Stella P R, Nathoe H, Kirkels H, Hamer B, Meijburg H W, Doevendans P A. Stent thrombosis in real-world patients: a comparison of drug-eluting with bare metal stents. Neth Heart J. 2007; 15 (11):382-386.

Colombo A, Chieffo A. Drug-eluting stent update 2007: Part III: Technique and unapproved/unsettled indications (left main, bifurcations, chronic total occlusions, small vessels and long lesions, saphenous vein grafts, acute myocardial infarctions, and multivessel disease). Circulation. 2007; 116:1424-1432.

Wessely R, Schomig A, Kastrati A. Sirolimus and Paclitaxel on polymer-based drug-eluting stents: similar but different. J Am Coll Cardiol. 2006; 47 (4):708-714.

Kolodgie F D, John M, Khurana C, Farb A, Wilson P S, Acampado E, Desai N, Soon-Shiong P, Virmani R. Sustained reduction of in-stent neointimal growth with the use of a novel systemic nanoparticle paclitaxel. Circulation. 2002; 106:1195-1198.

Morice M C, Serruys P W, Sousa J E, Fajadet J, Ban Hayashi E, Perin M, Colombo A, Schuler G, Barragan P, Guagliumi G, Molnar F, Falotico R. A randomized comparison of a sirolimus-eluting stent with a standard stent for coronary revascularization. N Engl J Med. 2002; 346 (23):1773-1780.

Moses J W, Leon M B, Popma J J, Fitzgerald P J, Holmes D R, O'Shaughnessy C, Caputo R P, Kereiakes D J, Williams D O, Teirstein P S, Jaeger J L, Kuntz R E. Sirolimus-eluting stents versus standard stents in patients with stenosis in a native coronary artery. N Engl J Med. 2003; 349 (14):1315-1323.

Roiron C, Sanchez P, Bouzamondo A, Lechat P, Montalescot G. Drug eluting stents: an updated meta-analysis of randomised controlled trials. Heart. 2006; 92 (5):641-649.

Babapulle M N, Joseph L, Belisle P, Brophy J M, Eisenberg M J. A hierarchical Bayesian meta-analysis of randomised clinical trials of drug-eluting stents. Lancet. 2004; 364 (9434):583-591.

Camenzind E, Steg P G, Wijns W. Stent thrombosis late after implantation of first-generation drug-eluting stents. Circulation. 2007; 7 (115):1440-1455.

Webster M W, Ormiston J A. Drug-eluting stents and late stent thrombosis. Lancet. 2007; 370 (9591):914-915.

Van Belle E, Susen S, Jude B, Bertrand M E. Drug-eluting stents: trading restenosis for thrombosis? J Thromb Haemost. 2007; 5 Suppl 1:238-245.

Jaffe R, Strauss B H. Late and very late thrombosis of drug-eluting stents. J Am Coll Cardiol. 2007; 50 (2):119-127.

Leon M B. Late thrombosis a concern with drug-eluting stents. J Interv Cardiol. 2007; 20 (1):26-29.

Zimarino M, Renda G, De Caterina R. Optimal duration of antiplatelet therapy in recipients of coronary drug-eluting stents. Drugs. 2005; 65 (6):725-732.

Win H K, Caldera A E, Maresh K, Lopez J, Rihal C S, Parikh M A, Granada J F, Marulkar S, Nassif D, Cohen D J, Kleiman N S. Clinical outcomes and stent thrombosis following off-label use of drug-eluting stents. JAMA. 2007; 297 (18):2001-2009.

Melikian N, Wijns W. Drug-eluting stents: a critique. Heart. 2008; 94:145-152

Rao S V, Shaw R E, Brindis R G, Klein L W, Weintraub W S, Peterson E D. On- versus off-label use of drug-eluting coronary stents in clinical practice (report from the American College of Cardiology National Cardiovascular Data Registry [NCDR]). Am J Cardiol. 2006; 97 (10):1478-1481.

Finn A, Nakazawa G, Joner M, Kolodogie F, Mont E, Gold H, Virmani R. Vascular responses to drug eluting stents: importance of delayed healing. Arterioscler Thromb Vasc Biol. 2007; 27 (7):1500-1510.

Kotani J, Awata M, Nanto S, Uematsu M, Oshima F, Minamiguchi H, GS GSM, Nagata S. Incomplete neointimal coverage of sirolimus-eluting stents: angioscopic findings. J Am Coll Cardiol 2006; 47 (10):2108-2111.

Jaffe R, Strauss B H. Late and very late thrombosis of drug-eluting stents: evolving concepts and perspectives. J Am Coll Cardiol. 2007; 50 (2):119-127.

Marin J, Rodriguez-Martinez M A. Role of vascular nitric oxide in physiological and pathological conditions. Pharmacol Ther. 1997; 75 (2):111-134.

Kuo P C, Schroeder R A. The emerging multifaceted roles of nitric oxide. Ann Surg. 1995; 221 (3):220-235.

Davies K M, Wink D A, Saavedra J E, Keefer L K. Chemistry of the diazeniumdiolates. 2. kinetics and mechanism of dissociation to nitric oxide in aqueous solution. J Am Chem Soc. 2001; 123:5473-5481.

Beckman J S. The physiological and pathological chemistry of nitric oxide. In: Jr. JRL, ed. Nitric Oxide: Principles and Actions. Sand Diego: Academic Press Inc.; 1996:1-71.

Reynolds M M, Frost M C, Meyerhoff M E. Nitric oxide-releasing hydrophobic polymers: preparation, characterization, and potential biomedical applications. Free Radic Biol Med. 2004; 37 (7):926-936.

Verma S, Marsden P. Nitric oxide-eluting polyurethanes-vascular grafts of the future? New Engl J Med. 2005; 353 (7):730-731.

Pulfer S K, Ott D, Smith D J. Incorporation of nitric oxide-releasing crosslinked polyethyleneimine microspheres into vascular grafts. J Biomed Mater Res. 1997; 37 (2):182-189.

Do Y, Kao E, Ganaha F, Minamiguchi H, Sugimoto K, Lee J, Elkins C, Amabile P, Kuo M, Wang D, Waugh J, Dake M. In-stent restenosis limitation with stent-based controlled-release nitric oxide: Initial results in rabbits. Radiology. 2004; 230:377-382.

Hou D, Narciso H, Kamdar K, Zhang P, Barclay B, March K L. Stent-based nitric oxide delivery reducing neointimal proliferation in a porcine carotid overstretch injury model. Cardiovasc Intervent Radiol. 2005; 28 (1):60-65.

Ziche M, Morbidelli L, Masini E, Amerini S, Granger H J, Maggi C A, Geppetti P, Ledda F. Nitric oxide mediates angiogenesis in vivo and endothelial cell growth and migration in vitro promoted by substance P. J Clin Invest. 1994; 94 (5):2036-2044.

Kawasaki K, Smith R S, Jr., Hsieh C M, Sun J, Chao J, Liao J K. Activation of the phosphatidylinositol 3-kinase/protein kinase Akt pathway mediates nitric oxide-induced endothelial cell migration and angiogenesis. Mol Cel Biol. 2003; 23 (16):5726-5737.

Aicher A, Heeschen C, Mildner-Rihm C, Urbich C, Ihling C, Technau-Ihling K, Zeiher A M, Dimmeler S. Essential role of endothelial nitric oxide synthase for mobilization of stem and progenitor cells. Nat Med. 2003; 9 (11):1370-1376.

Lipke E A, West J L. Localized delivery of nitric oxide from hydrogels inhibits neointima formation in a rat carotid balloon injury model. Acta Biomaterialia. 2005; 1 (6):597-606.

Miller M, Megson I. Recent developments in nitric oxide donor drugs. Br J Pharmacol. 2007; 151 (3):305-321.

Hanson S R, Hutsell T C, Keefer L K, Mooradian D L, Smith D J. Nitric oxide donors: a continuing opportunity in drug design. Adv Pharmacol. 1995; 34:383-398.

Miller M, Megson I. Recent developments in nitric oxide donor drugs. Br J Pharmacol. 2007; 151:305-321.

Gori T, Parker J D. The puzzle of nitrate tolerance: pieces smaller than we thought? Circulation. 2002; 106 (18):2404-2408.

Paramonov S E, Jun H W, Hartgerink J D. Self-assembly of peptide-amphiphile nanofibers: the roles of hydrogen bonding and amphiphilic packing. J Am Chem Soc. 2006; 128:7291-7298.

Saavedra J, Fitzhugh A, Keefer L. Chapter 24: Diazeniumdiolates (Formerly NONOates) in Cardiovscular Research and Potential Clinical Applications. In: Loscalzo J, Vita J A, eds. Nitric oxide and the cardiovascular system. Totowa, N.J.: Humana Press; 2000.

Keefer L K, Nims R W, Davies K M, Wink D A. "NONOates" (1-substituted diazen-1-ium-1,2-diolates) as nitric oxide donors: convenient nitric oxide dosage forms. Methods Enzymol. Vol 268; 1996:281-293.

Hrabie J A, Keefer L K. Chemistry of the nitric oxide-releasing diazeniumdiolate ("nitrosohydroxylamine") functional group and its oxygen-substituted derivatives. Chem Rev. 2002; 102 (4):1135-1154.

Jun H, West J. Modification of polyurethaneurea with PEG and YIGSR peptide to enhance endothelialization without platelet adhesion. J Biomed Mater Res PartB: Appl Biomater. 2005; 72B:131-139.

Bohl K S, West J L. Nitric oxide-generating polymers reduce platelet adhesion and smooth muscle cell proliferation. Biomaterials. 2000; 21:2273-2278.

Jun H W, Taite L J, West J L. Nitric oxide-producing polyurethanes. Biomacromolecules. 2005; 6:838-844.

W. P. M. Lowik D, Hest J C M v. Peptide based amphiphiles. Chem Soc Rev. 2004; 33:234-245.

Jun H W, Paramonov S, Hartgerink J D. Synthetic ECM mimics. Soft Matter. 2006; 2:177-181.

Hartgerink J D, Baniash E, Stupp S I. Peptide-amphiphile nanofibers: A versatile scaffold for the preparation of self-assembling materials. Proc Natl Acad Sci. 2002; 99 (8): 5133-5138.

Hartgerink J D, Beniash E, Stupp S I. Self-assembly and mineralization of peptide-amphiphile nanofibers. Science. 2001; 294:1684-1688.

Jun H W, Yuwono V, Paramonov S E, Hartgerink J D. Enzyme-mediated degradation of peptide-amphiphile nanofiber networks. Adv Mater. 2005; 17:2612-2617.

Paramonov S E, Jun H W, Hartgerink J D. Self-assembly of peptide-amphiphile nanofibers: the roles of hydrogen bonding and amphiphilic packing. J Am Chemical Soc. 2006; 128 (22):7291-7298.

Curtis A, Wilkinson C. Nanotechniques and approaches in biotechnology. Trends Biotechnol. 2001; 19 (3):97-101.

Barnes C P, Sell S A, Boland E D, Simpson D G, Bowlin G L. Nanofiber technology: designing the next generation of tissue engineering scaffolds. Adv Drug Deliv Rev. 2007; 59 (14): 1413-1433.

Malkar N B, Lauer-Fields J L, Juska D, Fields G B. Characterization of peptide-amphiphiles possessing cellular activation sequences. Biomacromolecules. 2003; 4 (3):518-528.

Hosseinkhani H, Hosseinkhani M, Khademhosseini A, Kobayashi H, Tabata Y. Enhanced angiogenesis through controlled release of basic fibroblast growth factor from peptide amphiphile for tissue regeneration. Biomaterials. 2006; 27 (34):5836-5844.

Rajangam K, Behanna H A, Hui M J, Han X, Hulvat J F, Lomasney J W, Stupp S I. Heparin binding nanostructures to promote growth of blood vessels. Nano Lett. 2006; 6 (9):2086-2090.

Hosseinkhani H, Hosseinkhani M, Tian F, Kobayashi H, Tabata Y. Bone regeneration on a collagen sponge self-assembled peptide-amphiphile nanofiber hybrid scaffold. Tissue Eng. 2007; 13(1):11-19.

Hosseinkhani H, Hosseinkhani M, Tian F, Kobayashi H, Tabata Y. Ectopic bone formation in collagen sponge self-assembled peptide-amphiphile nanofibers hybrid scaffold in a perfusion culture bioreactor. Biomaterials. 2006; 27 (29):5089-5098.

Sargeant T D, Guler M O, Oppenheimer S M, Mata A, Satcher R L, Dunand D C, Stupp S I. Hybrid bone implants: self-assembly of peptide amphiphile nanofibers within porous titanium. Biomaterials. 2008; 29 (2):161-171.

Jun H, West J. Development of a YIGSR-peptide-modified polyurethaneurea to enhance endothelialization. J Biomater Sci Polymer Edn. 2004; 15 (1):73-94.

Giannelli G, Falk-Marzillier J, schiraldi O, Stetler-Stevenson W G, Quaranta V. Induction of cell migration by matrix metallopretease-2 cleavage of laminin-5. Science. 1997; 277:225-228.

Beck K, Hunter I, Engel J. Structure and function of laminin: anatomy of a multidomain glycoprotein. Faseb J. 1990; 4 (2):148-160.

Hubbell J A, Massia S P, Desai N P, Drumheller P D. Endothelial cell-selective materials for tissue engineering in the vascular graft via a new receptor. Bio/Technology. 1991; 9:568-572.

Massia S P, Rao S S, Hubbell J A. Covalently immobilized laminin peptide Tyr-Iie-Gly-Ser-Arg (YIGSR) supports cell spreading and co-localization of the 67-kilodalton laminin receptor with a-actin and vinculin. J Biol Chem. 1993; 268:8053-8059.

Massia S P, Hubbell J A. Human endothelial cell interactions with surface-coupled adhesion peptides on a nonadhesive glass substrate and two polymeric biomaterials. J Biomed Mater Res. 1991; 25 (2):223-242.

Fittkau M H, Zilla P, Bezuidenhout D, Lutolf M P, Human P, Hubbell J A, Davies N. The selective modulation of endothelial cell mobility on RGD peptide containing surfaces by YIGSR peptides. Biomaterials. 2005; 26 (2):167-174.

Taite L J, Yang P, Jun H W, West J L. Nitric oxide-releasing polyurethane-PEG copolymer containing the YIGSR peptide promotes endothelialization with decreased platelet adhesion. J Biomed Mater Res B Appl Biomater. 2008; 84 (1):108-116.

Liuzzo J P, Ambrose J A, Coppola J T. Sirolimus- and taxol-eluting stents differ towards intimal hyperplasia and re-endothelialization. J Invasive Cardiol. 2005; 17 (9):497-502.

Steffel J, Tanner F C. Biological effects of drug-eluting stents in the coronary circulation. Herz. 2007; 32 (4):268-273.

Kroncke K D, Fehsel K, Kolb-Bachofen V. Nitric oxide: cytotoxicity versus cytoprotection—how, why, when, and where? Nitric Oxide. 1997; 1 (2):107-120.

Chen K, Pittman R N, Popel A S. Nitric oxide in the vasculature: where does it come from and where does it go? A quantitative perspective. Antioxid Redox Signal. 2008; 10 (7):1185-1198.

Kaul S, Makkar R R, Nakamura M, Litvack F I, Shah P K, Forrester J S, Hutsell T C, Eigler N L. Inhibition of acute stent thrombosis under high-shear flow conditions by a nitric oxide donor, DMHD/NO. An ex vivo porcine arteriovenous shunt study. Circulation. 1996; 94 (9):2228-2234.

I. Sequences

1.
                              SEQ ID NO: 1
Gly-Thr-Ala-Gly-Leu-Ile-Gly-Gln

2.
                              SEQ ID NO: 2
Tyr-Ile-Gly-Ser-Arg

3.
                              SEQ ID NO: 3
Lys-Lys-Lys-Lys-Lys

4.
                              SEQ ID NO: 4
Gly-Thr-Ala-Gly-Leu-Ile-Gly-Gln-Tyr-Ile-Gly-Ser-Arg

5.
                              SEQ ID NO: 5
Gly-Thr-Ala-Gly-Leu-Ile-Gly-Gln-Lys-Lys-Lys-Lys-Lys

6.
                              SEQ ID NO: 6
Gly-Thr-Ala-Gly-Leu-Ile-Gly-Gln-Tyr-Ile-Gly-Ser-Arg-Lys-Lys-Lys-Lys-Lys

7.
                              SEQ ID NO: 7
Gly-Thr-Ala-Gly-Leu-Ile-Gly-Gln-Lys-Lys-Lys-Lys-Lys-Tyr-Ile-Gly-Ser-Arg

-continued

8. SEQ ID NO: 8
Arg-Gly-Asp

9. SEQ ID NO: 9
Arg-Gly-Asp-Ser

10. SEQ ID NO: 10
Asp-Gly-Glu-Ala

11. SEQ ID NO: 11
Val-Ala-Pro-Gly

12. SEQ ID NO: 12
Arg-Glu-Asp-Val

13. SEQ ID NO: 13
Asp-Gly-Glu-Ala

14. SEQ ID NO: 14
Lys-Arg-Ser-Arg

15. SEQ ID NO: 15
Gly-Pro-Gln-Gly-Leu-Leu-Gly

16. SEQ ID NO: 16
Gly-Pro-Gly-Ile-Trp-Gly-Gln

17. SEQ ID NO: 17
Cys-Cys-Cys-Cys-Cys

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A peptide amphiphile, comprising a hydrophilic peptide sequence and a hydrophobic tail, wherein the hydrophilic peptide sequence comprises a degradation sequence and one or more of a first cell adhesive sequence and a nitric oxide producing donor sequence; wherein the first adhesive sequence is an endothelial cell adhesive sequence; wherein the cell adhesive sequence comprises YIGSR (SEQ ID NO: 2), RGD (SEQ ID NO: 8), RGDS (SEQ ID NO: 9), DGEA (SEQ ID NO: 10), VAPG (SEQ ID NO: 11), REDV (SEQ ID NO: 12), or LRSR (SEQ ID NO: 14); wherein the degradation sequence comprises a matrix metalloprotease (MMP) specific cleavage site; and wherein the nitric oxide producing sequence comprises polylysine, polycysteine sequence, or modified polylysine.

2. The peptide amphiphile of claim 1, wherein the hydrophilic peptide sequence comprises the formula:

DS - - - CA, wherein - - - is a direct or indirect covalent linkage,
wherein "DS" is a degradation sequence; and
wherein "CA" is an endothelial cell adhesive sequence.

3. The peptide amphiphile of claim 1, wherein the hydrophilic peptide sequence comprises the formula:

DS - - - KK, wherein - - - is a direct or indirect covalent linkage,
wherein "DS" is a degradation sequence; and
wherein "KK" is a nitric oxide producing donor sequence.

4. The peptide amphiphile of claim 1, wherein the hydrophilic peptide sequence comprises the formula:

DS - - - CA - - - KK, wherein - - - is a direct or indirect covalent linkage,
wherein "DS" is a degradation sequence;
wherein "CA" is an endothelial cell adhesive sequence; and
wherein "KK" is a nitric oxide producing donor sequence.

5. The peptide amphiphile of claim 1, wherein the hydrophilic peptide sequence comprises the formula:

DS - - - KK - - - CA, wherein - - - is a direct or indirect covalent linkage,
wherein "DS" is a degradation sequence;
wherein "CA" is an endothelial cell adhesive sequence; and
wherein "KK" is a nitric oxide producing donor sequence.

6. The peptide amphiphile of claim 1, wherein the degradation sequence comprises a sequence that undergoes cell-mediated protelytic degradation.

7. The peptide amphiphile of claim 6, wherein the degradation sequence comprises a matrix metalloprotease (MMP) specific cleavage site.

8. The peptide amphiphile of claim 7, wherein the degradation sequence comprises a matrix metalloprotease-2 (MMP2) specific cleavage site.

9. A composition comprising a first and second peptide amphiphile, each independently comprising a hydrophilic peptide sequence and a hydrophobic tail, wherein the hydrophilic peptide sequence of the first peptide amphiphile comprises a degradation sequence and an endothelial cell adhesive sequence, wherein the degradation sequence comprises a matrix metalloprotease (MMP) specific cleavage site, and wherein the hydrophilic peptide sequence of the second peptide amphiphile comprises a degradation sequence and a nitric oxide producing donor sequence; wherein the cell adhesive sequence comprises YIGSR (SEQ ID NO: 2), RGD (SEQ ID NO: 8), RGDS (SEQ ID NO: 9), DGEA (SEQ ID NO: 10), VAPG (SEQ ID NO: 11), REDV (SEQ ID NO: 12), or LRSR (SEQ ID NO: 14); and wherein the nitric oxide producing sequence comprises polylysine, polycysteine sequence, or modified polylysine.

10. The composition of claim 9, wherein the hydrophilic peptide sequence of the first peptide amphiphile comprises the formula:

DS - - - CA, wherein each - - - is independently a direct or indirect covalent linkage,
wherein "DS" is a degradation sequence; and
wherein "CA" is an endothelial cell adhesive sequence;
and where the hydrophilic peptide sequence of the second peptide amphiphile comprises the formula:

DS - - - KK, wherein "KK" is a nitric oxide producing donor sequence.

11. An endothelium mimicking nanomatrix, comprising one or more peptide amphiphiles assembled into nanofibers, wherein the peptide amphiphiles each comprise a hydrophilic peptide sequence and a hydrophobic tail, wherein the hydrophilic peptide sequence comprises a degradation sequence and one or more of a first cell adhesive sequence and a nitric oxide producing donor sequence, and wherein the degradation sequence comprises a matrix metalloprotease (MMP) specific cleavage site wherein the cell adhesive sequence comprises YIGSR (SEQ ID NO: 2), RGD (SEQ ID NO: 8), RGDS (SEQ ID NO: 9), DGEA (SEQ ID NO: 10), VAPG (SEQ ID NO: 11), REDV (SEQ ID NO: 12), or LRSR (SEQ ID NO: 14); and wherein the nitric oxide producing sequence comprises polylysine, polycysteine sequence, or modified polylysine.

12. The endothelium mimicking nanomatrix of claim 11, wherein the nanofibers comprise a mixture of peptide amphiphiles having formulas DS - - - CA and DS - - - KK wherein "DS" is a degradation sequence; wherein "CA" is an endothelial cell adhesive sequence; and wherein "KK" is a nitric oxide producing donor sequence.

13. The endothelium mimicking nanomatrix of claim 12, wherein the DS - - - CA and DS - - - KK peptide amphiphiles are present in the nanofibers at a ratio of about 1:9 to about 9:1, wherein "DS" is a degradation sequence; and wherein "KK" is a nitric oxide producing donor sequence.

14. A composition comprising a medical device coated with an endothelium mimicking nanomatrix, comprising one or more peptide amphiphiles assembled into nanofibers, wherein the peptide amphiphiles each comprise a hydrophilic peptide sequence and a hydrophobic tail, wherein the hydrophilic peptide sequence comprises a degradation sequence and one or more of a first cell adhesive sequence and a nitric oxide producing donor sequence, wherein the first adhesive sequence is an endothelial cell adhesive sequence that does not bind to smooth muscle cells and/or platelets, and wherein the degradation sequence comprises a matrix metalloprotease (MMP) specific cleavage site; wherein the cell adhesive sequence comprises YIGSR (SEQ ID NO: 2), RGD (SEQ ID NO: 8), RGDS (SEQ ID NO: 9), DGEA (SEQ ID NO: 10), VAPG (SEQ ID NO: 11), REDV (SEQ ID NO: 12), or LRSR (SEQ ID NO: 14); and wherein the nitric oxide producing sequence comprises polylysine, polycysteine sequence, or modified polylysine.

15. The composition of claim 14, wherein the medical device is a vascular stent, vascular graft, catheter, pacemaker, or heart valve.

16. The peptide amphiphile of claim 1, wherein the cell adhesive sequence comprises YIGSR (SEQ ID NO: 2) and the nitric oxide producing sequence comprises polylysine.

17. The composition of claim 9, wherein the cell adhesive sequence comprises YIGSR (SEQ ID NO: 2) and the nitric oxide producing sequence comprises polylysine.

18. The endothelium mimicking nanomatrix of claim 11, wherein the cell adhesive sequence comprises YIGSR (SEQ ID NO: 2) and the nitric oxide producing sequence comprises polylysine.

19. The composition of claim 14, wherein the cell adhesive sequence comprises YIGSR (SEQ ID NO: 2) and the nitric oxide producing sequence comprises polylysine.

* * * * *

```
                       SEQUENCE LISTING

<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 1

Gly Thr Ala Gly Leu Ile Gly Gln
  1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 2

Tyr Ile Gly Ser Arg
  1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 3

Lys Lys Lys Lys Lys
  1               5

<210> SEQ ID NO 4
<211> LENGTH: 13
<212> TYPE: PRT
<213> ORGANISM: Artificial Sequence
```

```
<220> FEATURE:
<223> OTHER INFORMATION: Description of Artificial Sequence: Note =
      Synthetic Construct

<400> SEQUENCE: 4

Gly Thr Ala Gly Leu Ile Gly Gln Tyr Ile Gly Ser Arg
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 5

Gly Thr Ala Gly Leu Ile Gly Gln Lys Lys Lys Lys Lys
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 6

Gly Thr Ala Gly Leu Ile Gly Gln Tyr Ile Gly Ser Arg Lys Lys Lys
1               5                   10                  15

Lys Lys

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 7

Gly Thr Ala Gly Leu Ile Gly Gln Lys Lys Lys Lys Lys Tyr Ile Gly
1               5                   10                  15

Ser Arg

<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 8

Arg Gly Asp
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 9
```

```
Arg Gly Asp Ser
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 10

Asp Gly Glu Ala
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 11

Val Ala Pro Gly
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 12

Arg Glu Asp Val
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 13

Asp Gly Glu Ala
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 14

Lys Arg Ser Arg
1

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Note =
```

```
                        Synthetic Construct

<400> SEQUENCE: 15

Gly Pro Gln Gly Leu Leu Gly
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 16

Gly Pro Gly Ile Trp Gly Gln
  1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 17

Cys Cys Cys Cys Cys
  1               5
```